(12) United States Patent
Toraya et al.

(10) Patent No.: US 8,340,248 B2
(45) Date of Patent: Dec. 25, 2012

(54) X-RAY DIFFRACTION METHOD AND X-RAY DIFFRACTION APPARATUS

(75) Inventors: Hideo Toraya, Tachikawa (JP); Hisashi Konaka, Hamura (JP)

(73) Assignee: Rigaku Corporation, Akishima-Shi (JP)

( * ) Notice: Subject to any disclaimer, the term of this patent is extended or adjusted under 35 U.S.C. 154(b) by 279 days.

(21) Appl. No.: 12/729,375

(22) Filed: Mar. 23, 2010

(65) Prior Publication Data

US 2010/0246768 A1    Sep. 30, 2010

(30) Foreign Application Priority Data

Mar. 25, 2009   (JP) .................................. 2009-73254

(51) Int. Cl.
*G01N 23/20* (2006.01)
(52) U.S. Cl. ............................. 378/70; 378/71; 378/85
(58) Field of Classification Search ................ 378/71, 378/73, 75, 76, 82–85
See application file for complete search history.

(56) References Cited

U.S. PATENT DOCUMENTS

| | | | |
|---|---|---|---|
| 6,263,042 | B1 | 7/2001 | den Hartog et al. |
| 7,801,272 | B2 * | 9/2010 | Toraya .......................... 378/71 |
| 2009/0086921 | A1 | 4/2009 | Toraya |

FOREIGN PATENT DOCUMENTS

| | | |
|---|---|---|
| JP | 06-082398 A | 3/1994 |
| JP | 07-063897 A | 3/1995 |
| JP | 07-072298 A | 3/1995 |
| WO | WO 00/19187 A2 | 4/2000 |

OTHER PUBLICATIONS

H. Toraya et al; Journal of Synchrotron Radiation; 1996; vol. 3, pp. 75-83.
A.N. Fitch: Journal of Research of the National Institute of Standards and Technology, vol. 109, pp. 133-142; 2004.
European Search Report dated Jul. 22, 2010, issued in counterpart European Application No. EP 10003230.9.

\* cited by examiner

*Primary Examiner* — Jurie Yun
(74) *Attorney, Agent, or Firm* — Holtz, Holtz, Goodman & Chick, PC

(57) ABSTRACT

In an X-ray diffraction method, an X-ray parallel beam is incident on a sample, and diffracted X-rays from the sample are reflected at a mirror and thereafter detected by an X-ray detector. The reflective surface of the mirror is a combination of plural flat reflective surfaces, the respective centers of which are located on an equiangular spiral having a center that is located on a surface of the sample. The X-ray detector is one-dimensional position-sensitive in a plane parallel to the diffraction plane. X-rays that have been reflected at different flat reflective surfaces reach different points on the X-ray detector respectively. A correction is performed for separately recognizing different reflected X-rays that may have been reflected at the different flat reflective surfaces, and might be mixed with each other on the same detecting region of the X-ray detector.

6 Claims, 37 Drawing Sheets

$$y_{DB} = \tan\phi \cdot x \quad (1)$$

$$\frac{dy}{dx} = -\tan(\theta_0 - \phi) \quad (2)$$

$$\frac{y}{x} = \tan\phi \quad (3)$$

$$a = \tan\theta_0 \quad (4)$$

$$\frac{dy}{dx} = \frac{\frac{y}{x} - a}{1 + a\frac{y}{x}} \quad (5)$$

$$\ln\left[\frac{x}{r}\left(1 + \frac{y^2}{x^2}\right)^{1/2}\right] = -\frac{1}{a}\tan^{-1}\frac{y}{x} \quad (6)$$

$$\ln\left[\frac{x}{r}(1 + \tan^2\phi)^{1/2}\right] = -\frac{\phi}{\tan\theta_0} \quad (7)$$

Within a range of $-\pi/2 \leqq \phi \leqq \pi/2$, $$(1+\tan^2 \phi)^{-1/2} = \cos\phi \quad (8)$$

$$x = r \cdot \exp\left(-\frac{\phi}{\tan\theta_0}\right) \cos\phi \quad (9)$$

$$y = r \cdot \exp\left(-\frac{\phi}{\tan\theta_0}\right) \sin\phi \quad (10)$$

$$y_{tan} = -\tan\theta_0 (x-200) \quad (11)$$

$$A = r \cdot \exp\left(-\frac{\phi}{\tan\theta_0}\right) \qquad (12)$$

$$y = -\tan(2\theta_0 - \phi)(x - A\cos\phi) + A\sin\phi \qquad (13)$$

$$y = -\tan 2\theta_0 (x-r) \qquad (14)$$

$$x_p = r\frac{\sin 4\theta_0}{2}\left[\frac{1}{\tan\phi} + \tan 2\theta_0 - \exp\left(-\frac{\phi}{\tan\theta_0}\right)\frac{1}{\sin\phi}\right] \qquad (15)$$

FIG. 8

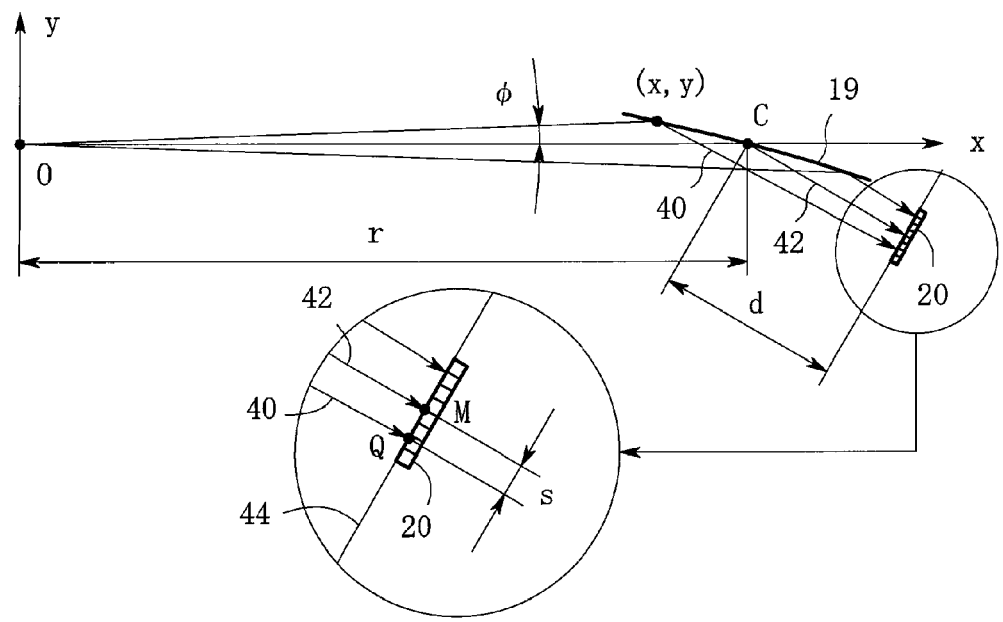

$$(x_m, y_m) = (r + d\cos2\theta_0, -d\sin2\theta_0) \qquad (16)$$

$$y = \frac{1}{\tan2\theta_0}[x-(r+d\cos2\theta_0)] - d\sin2\theta_0 \qquad (17)$$

$$x_q = \sin2\theta_0 \left[\tan\phi\,(d+r\cos2\theta_0) + \sin2\theta_0\left(\frac{A}{\cos\phi} - r\right)\right] + r + d\cos2\theta_0 \qquad (18)$$

$$y_q = \cos2\theta_0 \left[\tan\phi\,(d+r\cos2\theta_0) + \sin2\theta_0\left(\frac{A}{\cos\phi} - r\right)\right] - d\sin2\theta_0 \qquad (19)$$

$$s = \left|\tan\phi\,(d+r\cos2\theta_0) + \sin2\theta_0\left[\exp\left(-\frac{\phi}{\tan\theta_0}\right)\frac{1}{\cos\phi} - 1\right]r\right| \qquad (20)$$

$$y = A_i \tan \phi_i \cdot x \qquad (21)$$

$$A_i = r \cdot \exp\left(-\frac{\phi_i}{\tan \theta_0}\right) \qquad (22)$$

Channel number $$u_2 = \frac{\sin \beta}{\sin \alpha} B \qquad (23)$$

$$u_3 = \frac{\sin(\alpha + \beta)}{\sin \alpha} D \qquad (24)$$

$$u_4 = \frac{B \sin \beta + D \sin(\alpha + \beta)}{\sin \alpha} \qquad (25)$$

FIG. 16

$$I(u) \propto \int_0^B I \frac{\sin\alpha}{\sin\beta} \exp\left\{-\mu\left(\frac{1}{\sin\alpha}+\frac{1}{\sin\beta}\right)\frac{u\sin\alpha - b\sin\beta}{\sin(\alpha+\beta)}\right\} db \qquad (26)$$

$$I(u) \propto I \frac{\sin^2\alpha \cdot \sin(\alpha+\beta)}{\sin\beta(\sin\alpha+\sin\beta)} \frac{1}{\mu}(f_e - f_s) \qquad (27)$$

where, if $0 < u \leqq u_2$, $$f_e = 1$$

$$f_s = \exp\left\{-\mu \frac{\sin\alpha+\sin\beta}{\sin\beta \cdot \sin(\alpha+\beta)} u\right\} \; ;$$

if $u_2 < u \leqq u_3$, $$f_e = \exp\left\{-\mu \frac{(\sin\alpha+\sin\beta)(u\sin\alpha - B\sin\beta)}{\sin\alpha \cdot \sin\beta \cdot \sin(\alpha+\beta)}\right\}$$

$$f_s = \exp\left\{-\mu \frac{\sin\alpha+\sin\beta}{\sin\beta \cdot \sin(\alpha+\beta)} u\right\} \; ; \text{ and}$$

if $u_3 < u < u_4$, $$f_e = \exp\left\{-\mu \frac{(\sin\alpha+\sin\beta)(u\sin\alpha - B\sin\beta)}{\sin\alpha \cdot \sin\beta \cdot \sin(\alpha+\beta)}\right\}$$

$$f_s = \exp\left\{-\mu \frac{\sin\alpha+\sin\beta}{\sin\alpha \cdot \sin\beta} D\right\} \; .$$

Sample: $\alpha$-$SiO_2$    $SiO_2$ (1-10) plane

B = 0.8 mm, D = 0.5 mm, $\mu$ = 3.55 /mm $\alpha$ = 10.415 deg
$\beta$ = 10.415 deg Sample: $\alpha$-$SiO_2$    $SiO_2$ (221) plane B = 0.8 mm, D = 0.5 mm, $\mu$ = 3.55 /mm $\alpha$ = 39.955 deg
$\beta$ = 39.955 deg Diffraction intensity from first crystal

FIG. 27

Diffraction intensity from first crystal with trapezoidal approximation of left half If $N_{center} - w_{top} \leq N$, $$I(N) = BG + I_{top}. \tag{28}$$

If $N_{center} - w_{top} - w < N < N_{center} - w_{top}$, $$I(N) = BG + I_{top}\left[1 - \frac{N_{center} - w_{top} - N}{w}\right]. \tag{29}$$

If $N \leq N_{center} - w_{top} - w$, $$I(N) = BG. \tag{30}$$

Diffraction intensity from tenth crystal with trapezoidal approximation of right half If $N \leq N_{center} + w_{top}$, $$I(N) = BG + I_{top}. \tag{31}$$

If $N_{center} + w_{top} < N < N_{center} + w_{top} + w$, $$I(N) = BG + I_{top}\left[1 - \frac{N - N_{center} - w_{top}}{w}\right]. \tag{32}$$

If $N_{center} + w_{top} + w \leq N$, $$I(N) = BG. \tag{33}$$

FIG. 31

Diffraction intensity from first crystal with Gaussian approximation of left half $$I(N) = BG + I_{top} \exp\left(-\frac{(N_{center} - N)^2}{w^2}\right) \quad (34)$$

Diffraction intensity from tenth crystal with Gaussian approximation of right half $$I(N) = BG + I_{top} \exp\left(-\frac{(N - N_{center})^2}{w^2}\right) \quad (35)$$

FIG. 34

Diffraction intensity from first crystal
with approximation of left half
with a sum of Gaussian and Lorentzian $$I(N) = BG + I_{top}\left[\eta\left(1 + \frac{(N_{center} - N)^2}{w^2}\right)^{-1} + (1-\eta)\exp\left(-\ln 2 \cdot \frac{(N_{center} - N)^2}{w^2}\right)\right] \quad (36)$$

Diffraction intensity from tenth crystal
with approximation of right half
with a sum of Gaussian and Lorentzian $$I(N) = BG + I_{top}\left[\eta\left(1 + \frac{(N - N_{center})^2}{w^2}\right)^{-1} + (1-\eta)\exp\left(-\ln 2 \cdot \frac{(N - N_{center})^2}{w^2}\right)\right] \quad (37)$$

FIG. 37

Diffraction intensity from first crystal
with approximation of left half
with a combination of Gaussian and rectangle If $N_{center} - w_{top} \leq N$, $$I(N) = BG + I_{top}. \tag{38}$$

If $N < N_{center} - w_{top}$, $$I(N) = BG + I_{top} \exp\left(-\frac{(N_{center} - w_{top} - N)^2}{w^2}\right). \tag{39}$$

Diffraction intensity from tenth crystal
with approximation of right half
with a combination of Gaussian and rectangle If $N \leq N_{center} + w_{top}$, $$I(N) = BG + I_{top}. \tag{40}$$

If $N_{center} + w_{top} < N$, $$I(N) = BG + I_{top} \exp\left(-\frac{(N - N_{center} - w_{top})^2}{w^2}\right). \tag{41}$$

X-RAY DIFFRACTION METHOD AND X-RAY DIFFRACTION APPARATUS

BACKGROUND OF THE INVENTION

The present invention relates to an X-ray diffraction method and an X-ray diffraction apparatus with the use of the parallel beam method.

In the powder X-ray diffraction method for powder samples, thin film samples or polycrystalline samples, an analyzer must be inserted into a diffracted-beam-side optical system (i.e., a receiving optical system) in order to improve the angular resolution when using the parallel beam method. One of known analyzers is a long parallel slit that has a narrow angle of X-ray aperture, and the other is an analyzer crystal. The method with the long parallel slit is not so severe in X-ray intensity reduction but is inferior in angular resolution. On the contrary, the method with the analyzer crystal is superior in angular resolution but is severe in X-ray intensity reduction. Therefore, in the parallel beam method, there is desired a suitable analyzer that is superior in angular resolution and is small in X-ray intensity reduction.

An improvement in using the analyzer crystal and preventing the radiation intensity reduction in totality is known as disclosed in Journal of Synchrotron Radiation (1996), 3, 75-83 (which will be referred to as the first publication hereinafter) and Journal of Research of the National Institute of Standards and Technology, 109, 133-142 (2004) (which will be referred to as the second publication hereinafter).

The first publication discloses that plural (for example, six) X-ray detectors (which are scintillation counters) are located around a sample in the powder diffraction method using synchrotron orbit radiation. An analyzer crystal made of a Ge(111) flat plate is inserted between the sample and each of the X-ray detectors. The use of the plural X-ray detectors enables a short-time measurement of a diffraction pattern with a predetermined angular range as compared to the case using a single X-ray detector. Accordingly, the X-ray intensity reduction caused by the use of the analyzer crystals is prevented in totality of the apparatus.

The second publication discloses that, as well as the first publication, plural (for example, nine) analyzer crystals and as many X-ray detectors (scintillation counters) are located around a sample in the powder diffraction method.

By the way, the present invention is concerned with the use of a mirror having a reflective surface shaped in an equiangular spiral (a logarithmic spiral) in an X-ray diffraction apparatus with the parallel beam method. On the other hand, as to an X-ray diffraction apparatus with the focusing beam method, the use of a mirror (analyzing crystal) having an equiangular spiral reflective surface is disclosed in Japanese Patent Publication No. 6-82398 A (1994) (which will be referred to as the third publication hereinafter), Japanese Patent Publication No. 7-63897 A (1995) (which will be referred to as the fourth publication hereinafter), and Japanese Patent Publication No. 7-72298 A (1995) (which will be referred to as the fifth publication hereinafter).

The third publication discloses an analyzer crystal, which has a reflective surface shaped in a logarithmic spiral. The analyzer crystal is made of a synthetic multilayer lattice, in which the farther a point on the reflective surface is away from the X-ray source, the larger the lattice spacing is. The fourth publication discloses an X-ray spectrometer according to the second embodiment, which is composed of a combination of plural flat elements. Each flat element has a reflective point located on a curve that is nearly a logarithmic spiral. Each flat element is made of a synthetic multilayer lattice, in which the farther a point on the reflective surface is away from the X-ray source, the larger the lattice spacing is. The fifth publication discloses an X-ray spectroscopic element according to the fourth embodiment, which is composed of a combination of curved reflective surfaces with steps therebetween, each reflective surface having a longitudinal cross section close to a logarithmic spiral curve. Each reflective surface is made of a synthetic multilayer lattice, in which the farther the reflective surface is away from the X-ray source, the larger the lattice spacing is.

The structure that places plural analyzer crystals and plural X-ray detectors around a sample as disclosed in the first and second publications is so complex and expensive that it is hardly applicable to an X-ray diffraction method in a laboratory system.

The mirror having a reflective surface with a variable lattice spacing as disclosed in the third, fourth and fifth publications can not be used as a mirror, in the parallel beam method, for reflecting an X-ray beam having a different incident angle toward a different place.

SUMMARY OF THE INVENTION

It is an object of the present invention to provide an X-ray diffraction method and apparatus, which is superior in angular resolution, small in X-ray intensity reduction, and simple in structure as compared to the prior art using plural analyzer crystals and as many X-ray detectors.

It is another object of the present invention to provide an X-ray diffraction method and apparatus, which can restrain X-ray intensity reduction with remaining good angular resolution even when the width of an incident X-ray beam is comparatively large.

It is further another object of the present invention to provide an X-ray diffraction method and apparatus, in which when a reflective surface consists of a combination of plural flat reflective surfaces, adverse effects on measurement can be minimized, the adverse effects being that different reflected X-rays coming from adjacent flat reflective surfaces might be mixed each other.

In an X-ray diffraction method according to the present invention, an X-ray parallel beam is incident on a sample, and diffracted X-rays from the sample are reflected at a mirror using diffraction phenomena and thereafter detected by an X-ray detector. The mirror has a reflective surface consisting of a combination of plural flat reflective surfaces, which are located so that an angle (which is defined in a plane parallel to a diffraction plane) becomes constant among all the flat reflective surfaces, the angle being between each flat reflective surface and a line segment connecting a center of the each flat reflective surface and the sample, and further so that a crystal lattice plane that causes reflection is parallel to the each flat reflective surface. The X-ray detector is one-dimensional position-sensitive in a plane parallel to the diffraction plane, wherein a relative positional relationship between the flat reflective surfaces and the X-ray detector is determined, in a plane parallel to the diffraction plane, so that reflected X-rays that have been reflected at different flat reflective surfaces reach different points on the X-ray detector respectively. Different diffracted X-rays, which have been reflected at the mirror and have different diffraction angles, are detected by the X-ray detector distinctly and simultaneously. A corrective operation is performed for separately recognizing different reflected X-rays that have been reflected at the different flat reflective surfaces on an assumption that the different reflected X-rays that have been reflected at the different flat reflective surfaces might be unfortunately mixed each other on the same detecting region of the X-ray detector.

The respective centers of the flat reflective surfaces may preferably be located, in a plane parallel to the diffraction plane, on an equiangular spiral having a center that is located on a surface of the sample.

The corrective operation may preferably be carried out based on an intensity distribution curve of the diffracted X-rays along a beam width of the diffracted X-rays, the intensity distribution curve being made with a consideration of phenomena in which X-rays are diffracted at locations also below a surface of the sample. The intensity distribution curve may be made with at least a linear absorption coefficient $\mu$ of the sample, an incident angle $\alpha$ of the X-ray parallel beam on a surface of the sample, an outgoing angle $\beta$ of the diffracted X-rays from the surface of the sample, a thickness D of the sample, and a beam width B of the X-ray parallel beam.

In an X-ray diffraction apparatus according to the present invention, like the above-mentioned X-ray diffraction method invention, an X-ray parallel beam is incident on a sample, and diffracted X-rays from the sample are reflected at a mirror using diffraction phenomena and thereafter detected by an X-ray detector. The features about the reflective surface of the mirror, the X-ray detector, and the relative positional relationship between the mirror and the X-ray detector are all the same as those in the above-mentioned X-ray diffraction method invention. The X-ray diffraction apparatus further comprises means for performing a corrective operation for separately recognizing different reflected X-rays that have been reflected at the different flat reflective surfaces on an assumption that the different reflected X-rays that have been reflected at the different flat reflective surfaces might be unfortunately mixed each other on a same detecting region of the X-ray detector. The means for performing the corrective operation is realized specifically by a combination of processing functions of a computer program.

The present invention has an advantage that a combination of an analyzer crystal having a reflective surface with the predetermined shape and a single, one-dimensional position-sensitive X-ray detector brings a superior angular resolution, less reduction of an X-ray intensity, and a simple structure as compared to the prior art using plural analyzer crystals.

In addition, even when the width of an X-ray beam that is incident on a sample is comparatively large, the use of the mirror having a shape based on a new mathematical equation brings prevention of angular resolution reduction caused by X-ray optical aberration and prevention of X-ray intensity reduction, so that both a superior angular resolution and a superior X-ray intensity gain are attained.

Furthermore, with the present invention, when a reflective surface consists of a combination of plural flat reflective surfaces, adverse effects on measurement can be minimized, the adverse effects being that different reflected X-rays coming from adjacent flat reflective surfaces might be mixed each other.

BRIEF DESCRIPTION OF THE DRAWINGS

FIG. 8 shows an explanatory illustration indicating a positional relationship between the mirror and an X-ray detector and shows concerned mathematical equations;

FIG. 16 shows mathematical equations concerned in the state shown in FIG. 15;

FIG. 27 shows mathematical equations concerned in the trapezoidal approximation;

FIG. 31 shows mathematical equations concerned in the Gaussian approximation;

FIG. 34 shows mathematical equations concerned in the approximation with the sum of Gaussian and Lorentzian;

FIG. 37 shows mathematical equations concerned in the approximation with the combination of Gaussian and the rectangle.

DETAILED DESCRIPTION OF THE PREFERRED EMBODIMENTS

Figure 1:
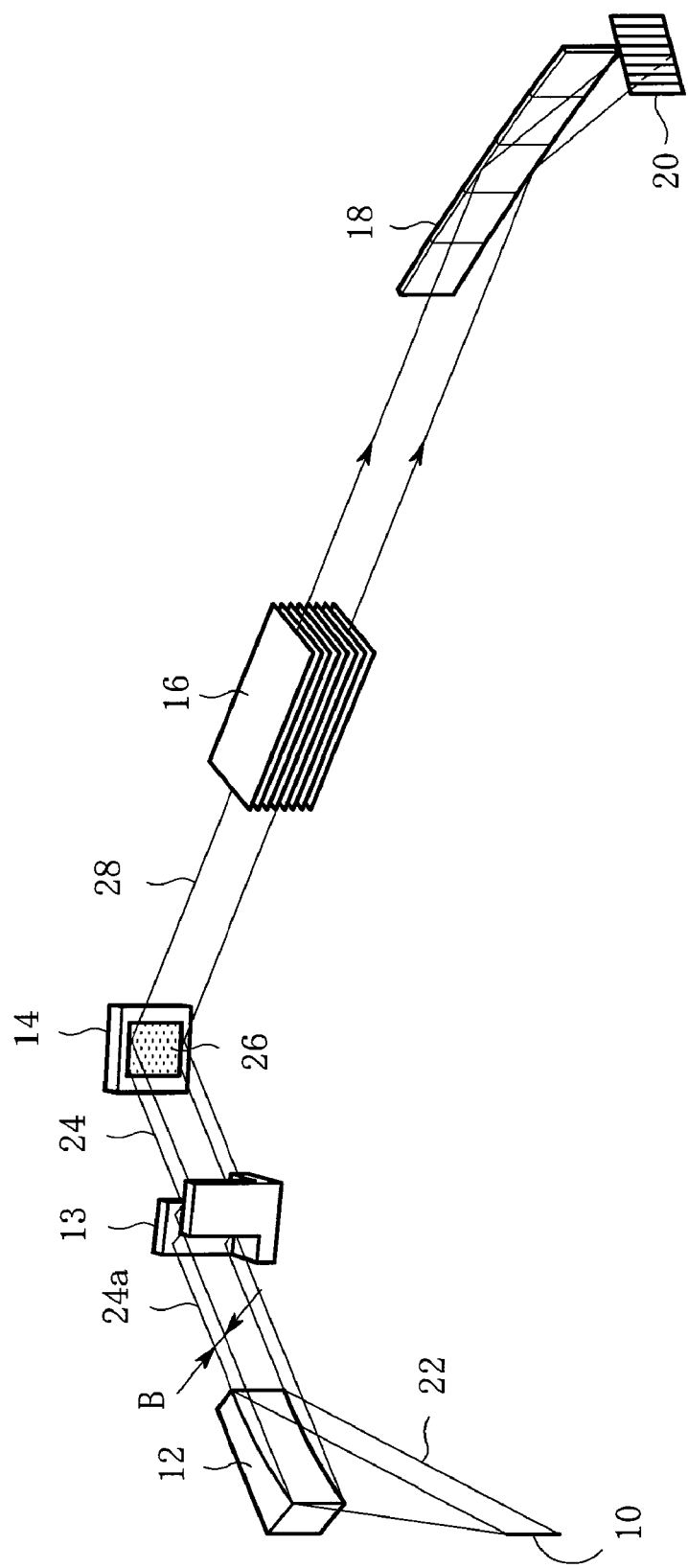
FIG. 1 is a schematic perspective view of an apparatus for carrying out an X-ray diffraction method according to the present invention.

Embodiments of the present invention will now be described in detail below with reference to the drawings. FIG. 1 is a schematic perspective view of an apparatus for carrying out an X-ray diffraction method according to the present invention. The X-ray diffraction apparatus comprises an X-ray source having a linear (or point-like) X-ray focus 10, a multilayer mirror 12 having a parabolic-shaped reflective surface, a channel cut monochromator 13 for selecting a characteristic X-ray Kα1, a sample holder 14, a Soller slit 16 for restricting vertical divergence of diffracted X-rays, a mirror 18 made of an analyzer crystal, and a one-dimensional position-sensitive X-ray detector 20. FIG. 1 shows the case using a linear X-ray focus. A divergent beam 22, which consists of X-rays emitted from the X-ray focus 10, is converted into a parallel beam 24a by the multilayer mirror 12 having a parabolic reflective surface. The multilayer mirror 12 is optimized for the X-ray wavelength to be used (CuKα1 in this embodiment) and has a gradient lattice spacing. The X-ray focus 10 is placed at a parabolic-focus position of the multilayer mirror 12. Assuming the use of a linear X-ray focus for example, the X-ray focus 10 is about ten millimeters long in the vertical direction. The parallel beam 24a passes through the channel cut monochromator 13 and the resultant parallel beam 24 (an incident X-ray) is incident on a sample 26. The parallel beam 24a and the parallel beam 24 after passing the channel-cut monochromator 13 have the same beam width B, which is approximately 0.84 millimeter in the horizontal plane. The sample 26 is powdery and the recess of the sample holder 14 is filled with the sample 26. Diffracted X-rays 28 will come from the sample 26. The diffracted X-rays 28 are restricted in vertical divergence by the Soller slit 16.

Figure 2:
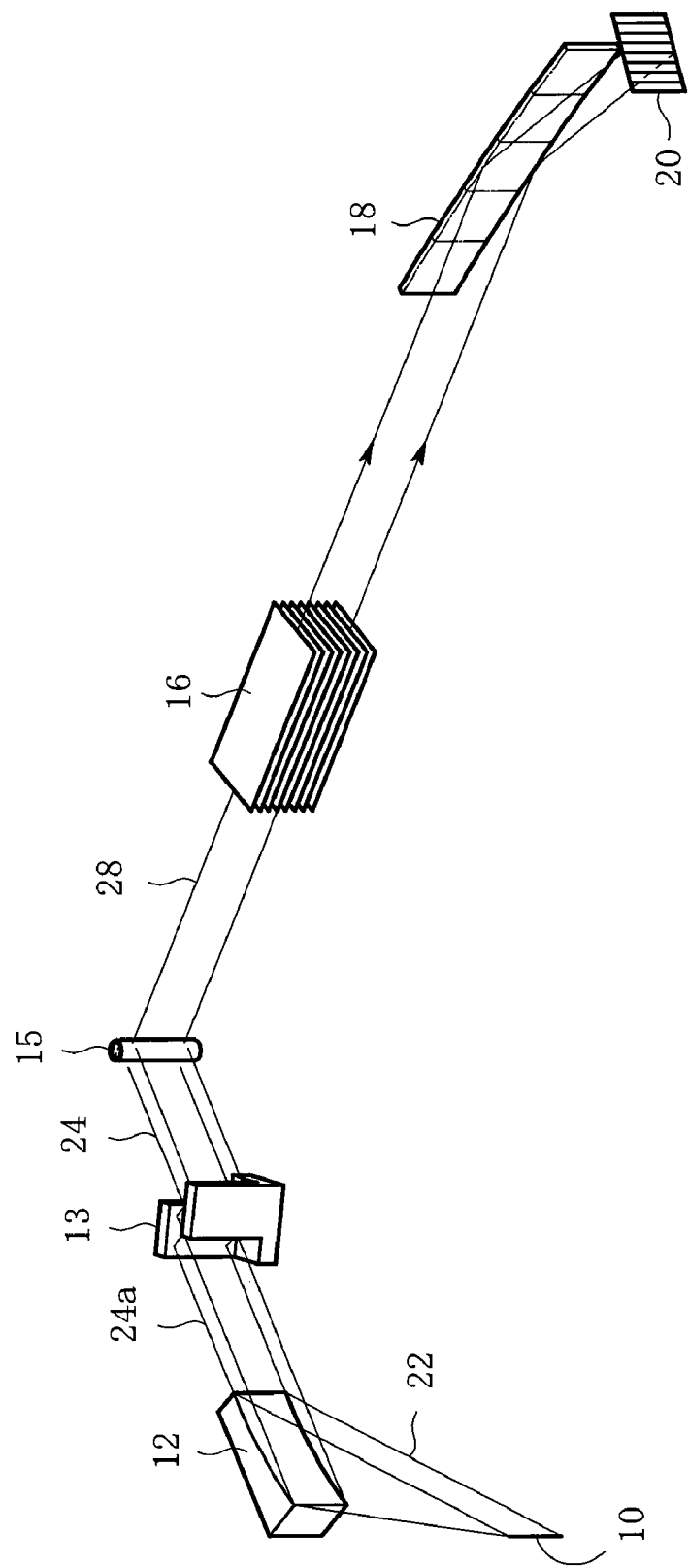
FIG. 2 is a schematic perspective view illustrating a modified optical system of the X-ray diffraction apparatus shown in FIG. 1.

The sample 26 is not limited to powder, but a polycrystalline substance (metal and so on), a thin film sample on a substrate, and a filament sample may be used. Any sample holder for so-called reflection-type X-ray diffraction analysis may be used. In addition, a sample holder for transmission-type X-ray diffraction analysis may be used: for example, as shown in FIG. 2, a capillary tube 15 may be filled with a sample.

Figure 3:
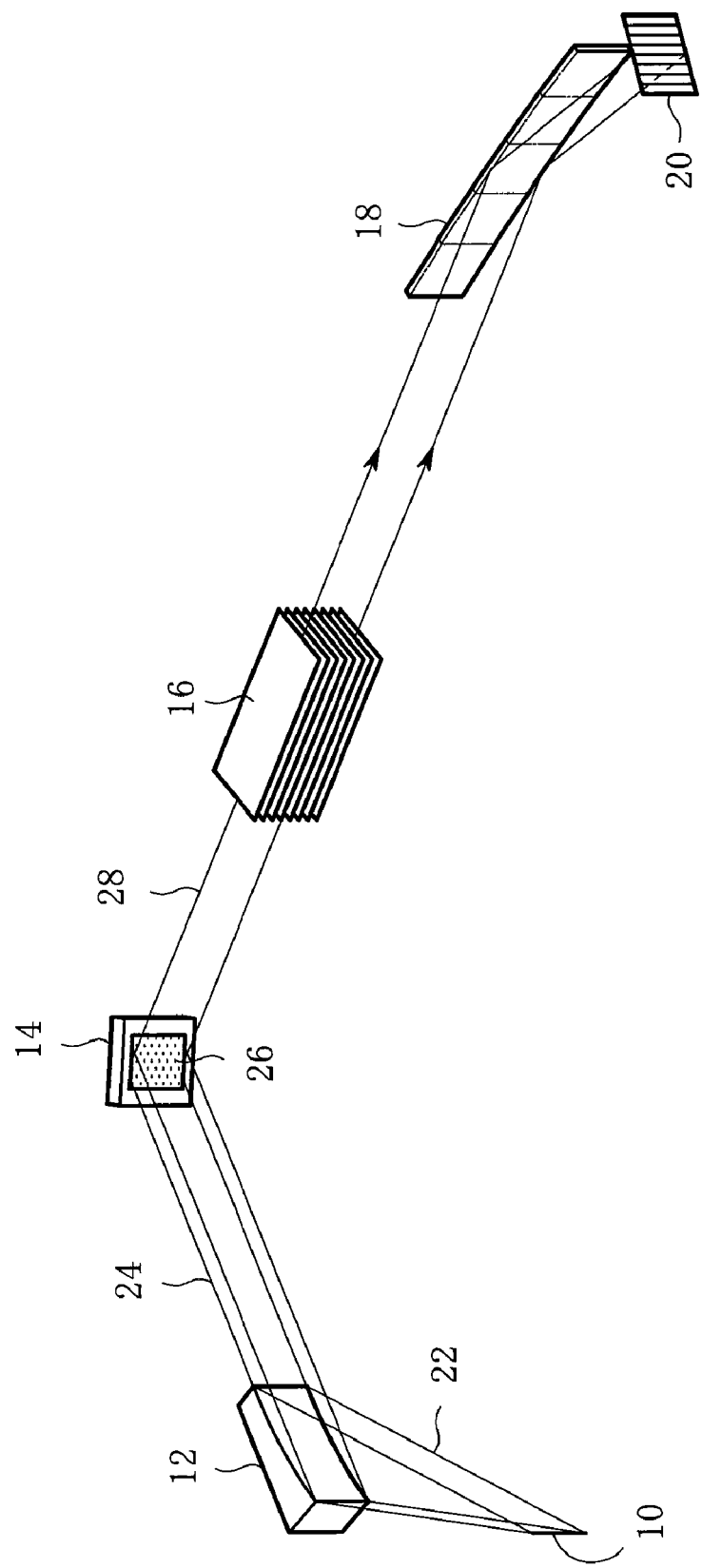
FIG. 3 is a schematic perspective view illustrating another modified optical system of the X-ray diffraction apparatus shown in FIG. 1.

FIG. 3 shows a modified optical system of the X-ray diffraction apparatus shown in FIG. 1. The modified embodiment differs from the apparatus shown in FIG. 1 in that the channel cut monochromator is omitted in the incident-side optical system, and the multilayer mirror 12 is optimized for the X-ray wavelength to be used in this embodiment (CuKα in this embodiment, i.e., the doublet of CuKα1 and CuKα2).

Referring back to FIG. 1, a plane including both the incident X-ray 24 and the diffracted X-ray 28 is generally called a diffraction plane or an equatorial plane. In this specification, the plane including both the incident X-ray 24 and the diffracted X-ray 28 is defined as the diffraction plane. An X-ray divergence in the diffraction plane is generally called an equatorial divergence or a radial divergence. In this specification, the divergence in the diffraction plane is called a horizontal divergence, whereas a divergence in a plane perpendicular to the diffraction plane is called a vertical divergence. In the optical system shown in FIG. 1, the diffraction plane exists in the horizontal plane, and the X-ray focus 10 stands upright, and the surface of the sample 26 also stands upright.

The Soller slit 16 restricts the vertical divergence. The horizontal divergence in the parallel beam method, which affects directly a resolution of the detected diffraction angle, is severely restricted by both the mirror 18 that will be described later and the channel cut monochromator 13 described above. The mirror 18 is a key component in the present invention, which guarantees a superior angular resolution of the diffracted X-ray 28: this feature will be explained in detail later. An approximate size of the mirror 18 is in a range between 15 and 20 millimeters in height and in a range between 60 and 80 millimeters in length. The channel cut monochromator 13 uses a Ge(220) lattice plane when the X-ray target is Cu.

The one-dimensional position-sensitive X-ray detector 20 uses a silicon strip detector (SSD) in this embodiment. The detector is one-dimensional position-sensitive in a plane parallel to the diffraction plane. That is to say, one upright elongated detective plane forms one detector channel, and many channels (for example, 128 channels) are arranged side by side in the horizontal direction. One channel has a size of, for example, 0.1 millimeter in width and 15 millimeters in length (height in FIG. 1).

Figure 4:
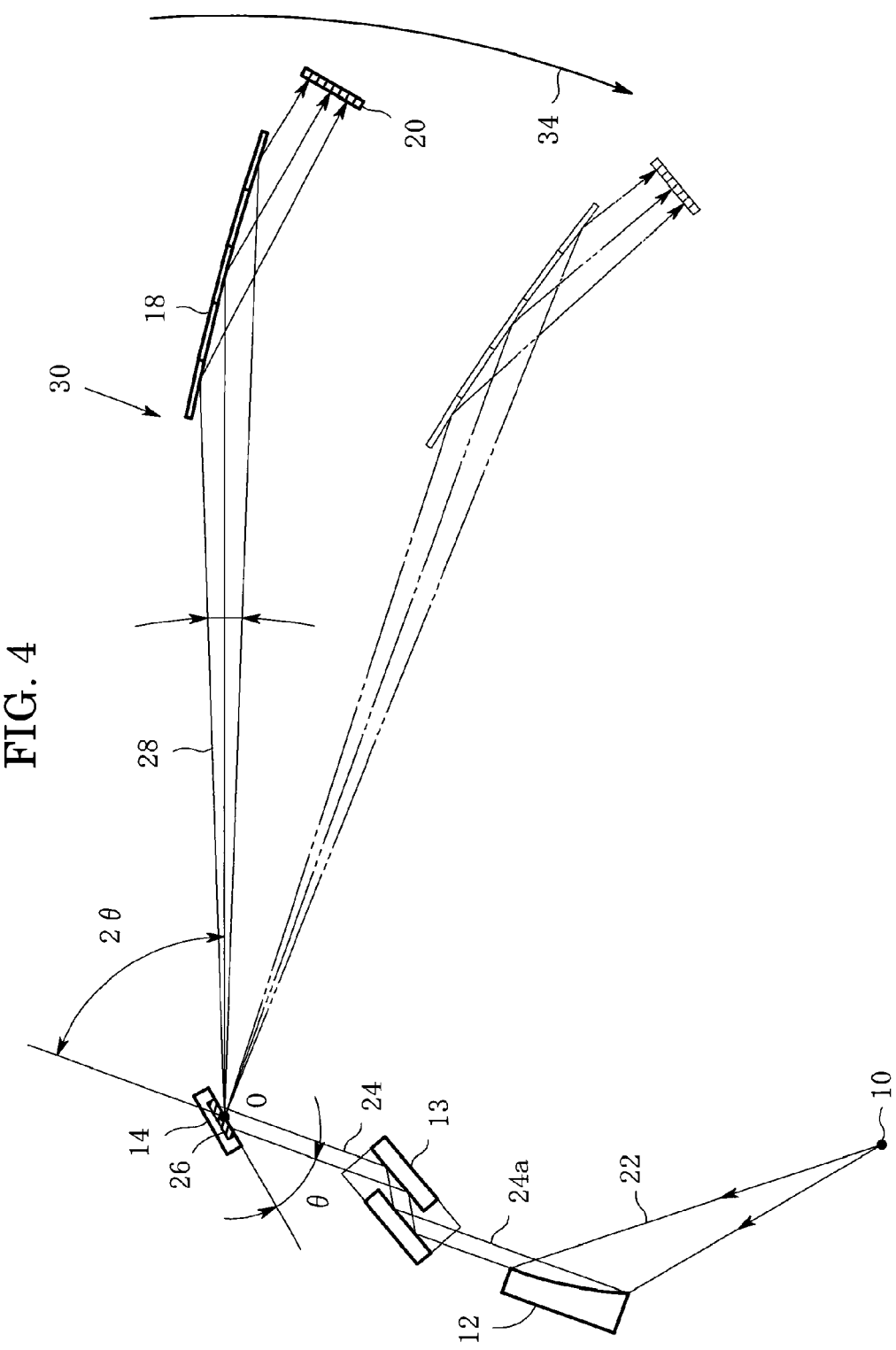
FIG. 4 is a plan view of the X-ray diffraction apparatus shown in FIG. 1.

FIG. 4 is a plan view of the X-ray diffraction apparatus shown in FIG. 1. An angle between the incident X-ray 24 and the diffracted X-ray 28 is 2θ. The angle θ is the Bragg angle of X-ray diffraction for the sample 26. When measuring a diffraction pattern with a predetermined angular range with the use of this X-ray diffraction apparatus, the sample holder 14 and a receiving optical system 30 rotate synchronously to keep a relationship between an angle θ of an incident X-ray 24 to a surface of the sample 26 and the angle 2θ described above into a ratio of 1 to 2. An X-ray diffraction pattern coming from the sample 26 is thus detected. The receiving optical system 30 consists mainly of the Soller slit 16 (see FIG. 1, it is omitted in FIG. 4), the mirror 18, and the X-ray detector 20, these optical components being mounted in a receiving arm (not shown). The receiving optical system 30 is, as indicated by an arrow 34, rotatable around the center of goniometer (point O). The surface of the sample 26 is located on the center of goniometer (point O).

Since the X-ray diffraction apparatus uses the parallel beam method, there is usable another measurement method that does not keep the relationship between θ and 2θ into the ratio of 1 to 2. Namely, when a diffraction pattern is measured with a predetermined angular range, the sample holder 14 may be kept stationary to keep the angle of the incident X-ray 24 to the surface of the sample 26 constant. Although the diffracted X-rays 28 from the sample 26 travel in different directions depending on the Bragg angles, those diffracted X-rays 28 can be detected with the use of the rotation of the receiving optical system 30.

Next, the shape of the reflective surface of the mirror 18 will be described in detail below. The mirror 18 is configured to combine plural flat reflective surfaces. In this embodiment, a partial mirror that constitutes each flat reflective surface is made of a single crystal of Ge, and it is formed so that Ge(111) plane is parallel to the flat reflective surface of the partial mirror. Each of the partial mirrors is to reflect, with the diffraction phenomena, the diffracted X-ray coming from the sample. The Ge(111) plane corresponds to the crystal lattice plane that causes diffraction.

Figure 5:
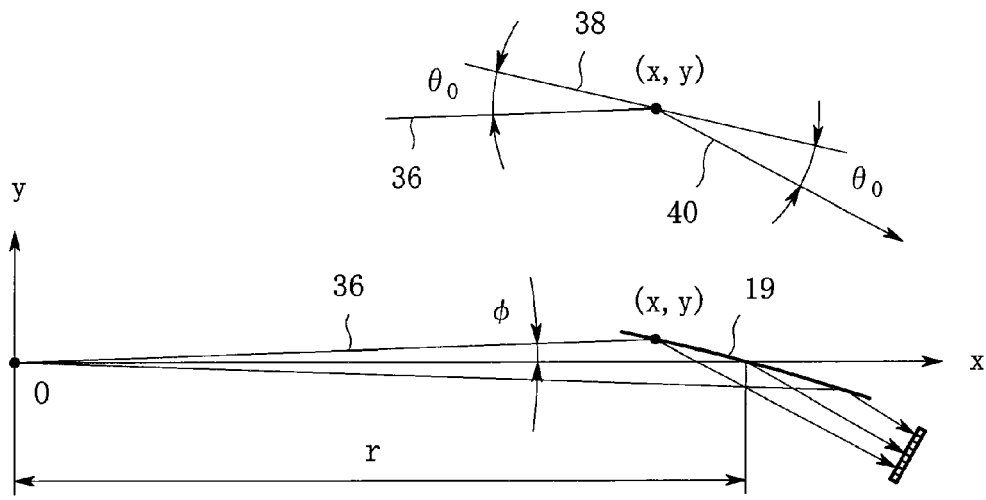
FIG. 5 shows an explanatory illustration for explaining how to obtain a shape of a reflective surface of a mirror and shows concerned mathematical equations.

The plural flat reflective surfaces are an improvement of one curved reflective surface, which will be explained first below. Referring to FIG. 5, the reflective surface 19 of the mirror has a shape of an equiangular spiral (which is also called a logarithmic spiral) in a plane parallel to the diffraction plane. FIG. 5 shows a view in a plane parallel to the diffraction plane. The feature of the equiangular spiral is that an angle $\theta_0$ between a tangential line 38 at any point (x, y) on the equiangular spiral and a line segment 36 that connects the any point (x, y) and the center of spiral (point O) is constant in any point on the spiral. It is the reason why the spiral is called "equiangular" spiral. The angle $\theta_0$ is set to be equal to the Bragg angle of Ge(111) for the X-ray wavelength to be used. In this embodiment, the mirror is made for CuKα1, and thus the angle $\theta_0$ is 13.64 degrees. The diffracted X-ray (that has been diffracted by the sample) that goes from the point O to the reflective surface is to be incident on the reflective surface 19 with an incidence angle $\theta_0$ to the tangential line 38 of the reflective surface 19 at any incident point on the reflective surface, so that the diffracted X-ray always satisfies the Bragg's condition. A reflected X-ray 40 that has reflected at the reflective surface 19 goes out with the angle $\theta_0$ to the tangential line 38 similarly.

The shape of the reflective surface 19 of the mirror can be determined as described below. Referring to FIG. 5, the center of goniometer (point O) is defined as the origin of the x-y coordinate system. The surface of the sample is located on the point O, and the center of the equiangular spiral is also located on the point O. It is assumed that the central region of the reflective surface 19 is located at a point of x=r on the x-axis. When a diffracted X-ray 36 travels in a direction at an angle φ (toward the counterclockwise direction) to the X-axis, the diffracted X-ray 36 reaches the point (x, y) on the reflective surface 19. The diffracted X-ray 36 may be expressed by equation (1) in FIG. 5, the coordinates (x, y) of each point on the diffracted X-ray track satisfying equation (1). Namely, y-coordinate of the diffracted X-ray, i.e., $y_{DB}$, is expressed with the angle φ and x-coordinate.

A slope dy/dx of the reflective surface 19 at the point (x, y) is expressed by equation (2). Equation (2) may be transformed into equation (5) with the use of equations (3) and (4). Equation (3) expresses a relationship between x-y coordinates at the point (x, y) and the angle φ. Equation (4) defines a tangent of the Bragg angle $\theta_0$ of the mirror as "a". Equation (5), which is a differential equation, is solved to obtain equation (6), which is transformed to equation (7).

Figure 6:
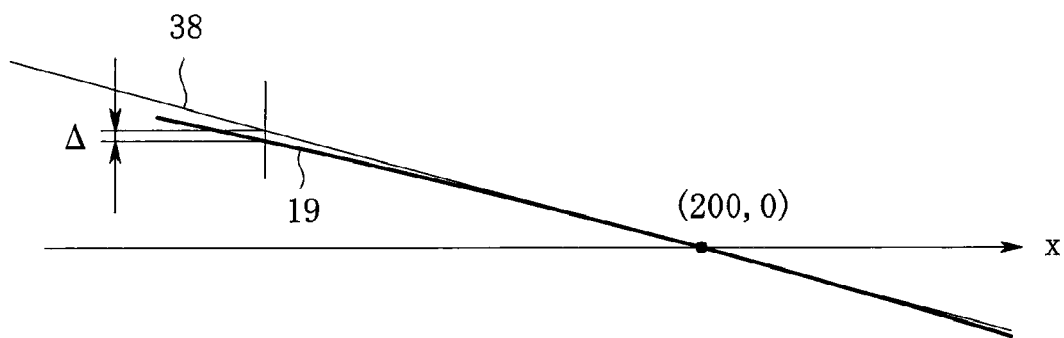
FIG. 6 shows an explanatory illustration of a shape of the reflective surface of the mirror and shows concerned mathematical equations.

A relationship shown in equation (8) in FIG. 6 is applied to equation (7) in FIG. 5, and the resultant equation is transformed to obtain equation (9) in FIG. 6. Equation (9) expresses the x-coordinate of any point (x, y) on the reflective surface 19. Thus, x-coordinate can be calculated with the use of the distance r, the angle φ, and the Bragg angle $\theta_0$. A combination of equations (9) and (3) brings equation (10), which gives y-coordinate. A combination of equations (9) and (10) defines the shape of the reflective surface 19 of the mirror.

In FIG. 6, how much the reflective surface of the mirror 19 is curved will be calculated below. Assuming that r is 200 millimeters, a distance Δ in y-direction between the tangential line 38 (which is a straight line) of the reflective surface 19 at the center (200, 0) of the reflective surface 19 and the reflective surface 19 (which is a curved line) can be calculated as described below. An equation of the tangential line 38 is expressed by equation (11) in FIG. 6. Y-coordinate on the tangential line is defined as $y_{tan}$. On the other hand, y-coordinate of the reflective surface 19 is expressed by equation (10). Table 1 shown below indicates the above-described distances Δ, which are calculated with the use of the angle φ as a parameter. For example, when φ is two degrees, x-coordinate on the reflective surface 19 is 173.099 millimeters and y-coordinate is 6.045 millimeters. Y-coordinate on the tangential line 38 at the same x-coordinate, i.e., $y_{tan}$, is 6.528 millimeters. Accordingly, subtracting y-coordinate of the reflective surface 19 from y-coordinate of the tangential line 38 brings 0.483 millimeter, which is the distance Δ. Similarly, there are also shown in the table the Δ values for φ being one degree, zero degree, negative one degree, and negative two degrees. Since y-coordinate of the reflective surface 19 is always less than y-coordinate of the tangential line when φ is increased and also decreased from zero degree, it is understood that the reflective surface 19 is slightly curved to be concave downward.

TABLE 1

| φ (°) | 2 | 1 | 0 | −1 | −2 |
|---|---|---|---|---|---|
| x (mm) | 173.099 | 186.092 | 200 | 214.882 | 230.801 |
| y (mm) | 6.045 | 3.248 | 0 | −3.751 | −8.060 |
| $y_{tan}$ (mm) | 6.528 | 3.375 | 0 | −3.611 | −7.474 |
| Δ (mm) | 0.483 | 0.127 | 0 | 0.140 | 0.586 |

Figure 7:
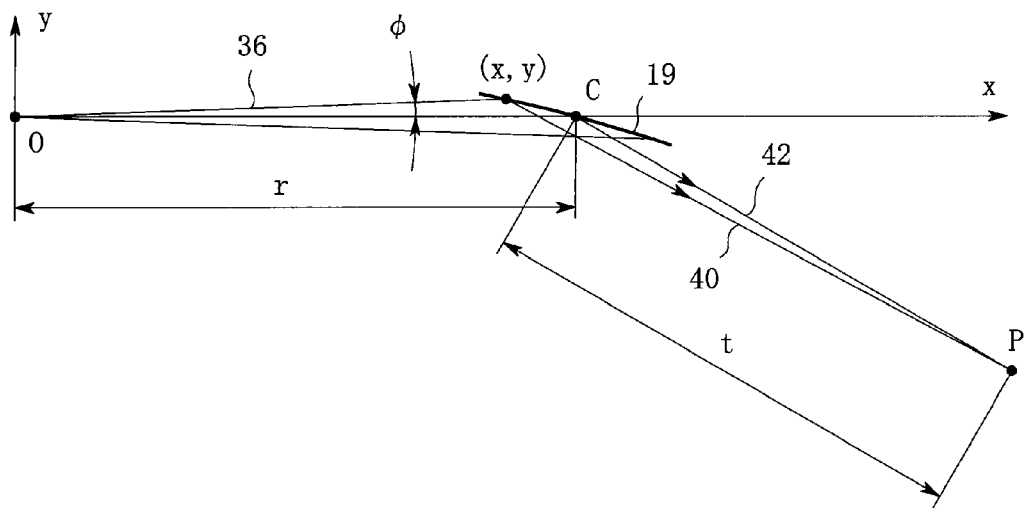
FIG. 7 shows an explanatory illustration indicating tracks of X-rays after reflected at the mirror and shows concerned mathematical equations.

Next, the track of an X-ray that has been reflected at the reflective surface will be described below. Referring to FIG. 7, the diffracted X-ray 36 that travels from the point O in a direction at the angle φ is reflected at the point (x, y) on the reflective surface 19 to become a reflected X-ray 40. On the other hand, the diffracted X-ray that travels from the point O along the x-axis is reflected at a point C on the reflective surface 19, the point C being an intersecting point of the reflective surface 19 and the x-axis, to become a reflected X-ray 42. The reflected X-ray 42 that has been reflected at the point C is to be called a central beam 42. A reflected X-ray 40 that has been reflected at any point (x, y) corresponding to the angle φ will intersect with the central beam 42 before long. The intersecting point is defined as a point P. A distance between the point C and the point P is defined as t.

In FIG. 7, an equation of the reflected X-ray 40 that has been reflected at any point (x, y) corresponding to the angle φ is expressed by equation (13). Symbol A in equation (13) is defined by equation (12). An equation of the central beam 42 is expressed by equation (14). The intersecting point P has coordinates that satisfy both equations (13) and (14) at once, and therefore x-coordinate that satisfies the both equations gives x-coordinate of the point P, i.e., $x_p$, which is expressed by equation (15). Y-coordinate of the point P, i.e., $y_p$, may be calculated, for example, by applying the obtained $x_p$ to equation (14).

Table 2 shown below indicates coordinates ($x_p$, $y_p$) of the point P and distances t, which are calculated with the use of the angle φ as a parameter, under the condition that r is 200 millimeters and $\theta_0$ is 13.64 degrees. It is understood, according to the table 2, that each reflected X-ray intersects with the central beam at a place approximately 200 millimeters away from the center (point C) of the reflective surface of the mirror. Accordingly, in order to distinctly detect different reflected X-rays that have been reflected at different points on the reflective surface with the position-sensitive X-ray detector, it is required to place the position-sensitive X-ray detector somewhere between the point C and the point P. In this embodiment, it is preferable to place the position-sensitive X-ray detector at a place approximately 50 to 100 millimeters away from the point C.

TABLE 2

| $\phi$ (°) | 2 | 1 | 0.5 | 0.1 | 0.01 |
|---|---|---|---|---|---|
| $x_p$ (mm) | 353.37 | 365.27 | 371.44 | 376.48 | 377.63 |
| $y_p$ (mm) | −79.09 | −85.23 | −88.41 | −91.01 | −91.60 |
| t (mm) | 172.56 | 185.95 | 192.89 | 198.56 | 199.86 |
| $\phi$ (°) | −0.01 | −0.1 | −0.5 | −1 | −2 |
| $x_p$ (mm) | 377.88 | 379.04 | 384.23 | 390.85 | 404.60 |
| $y_p$ (mm) | −91.73 | −92.33 | −95.01 | −98.42 | −105.51 |
| t (mm) | 200.14 | 201.45 | 207.29 | 214.73 | 230.20 |

Next, an angular separation function of the position-sensitive X-ray detector will be described below. Referring to FIG. 8, the detective plane of the position-sensitive X-ray detector 20 is placed away from the center (point C) of the reflective surface 19 of the mirror by a distance d. The detective plane is arranged nearly perpendicular to the central beam 42. The reflected X-ray 40 from the point (x, y) having the angle $\phi$ reaches a point Q on the detective plane. The central beam 42 from the point C reaches a point M on the detective plane. The distance between the point Q and the point M is s. Different reflected X-rays coming from plural different points on the reflective surface of the mirror are to reach plural different points on the X-ray detector respectively.

The coordinates $(x_m, y_m)$ of the point M is expressed by equation (16) in FIG. 8. An equation of a straight line 44 that represents the detective plane is expressed by equation (17). The point Q is an intersecting point of the straight line 44 with the reflected X-ray 40. Since the straight line 44 is expressed by equation (17) in FIG. 8 whereas the reflected X-ray 40 is expressed by equation (13) in FIG. 7, the coordinates $(x_q, y_q)$ of the point Q may be obtained by solving the two equations, leading to equations (18) and (19). The distance s between the points Q and M may be calculated with the use of equation (16) expressing the coordinates of the point M and equations (18) and (19) both expressing the coordinates of the point Q, leading to equation (20).

Table 3 shown below indicates distances s on the detective plane, which are calculated with the use of the angle $\phi$ as a parameter, under the condition that r is 200 millimeters, $\phi_0$ is 13.64 degrees, and d is 50 millimeters. When $\phi$ is two degrees, the point Q is 4.28 millimeters away from the point M, whereas when $\phi$ is negative two degrees, the point Q is 6.29 millimeters away from the point M in the opposite direction. Accordingly, assuming that the diffracted X-rays are captured by the mirror within a range between positive and negative two degrees in 2θ, i.e., within a range between positive and negative two degrees in $\phi$, the lateral size of the detector must be at least about ten millimeters when the detector is placed at a point of 50 millimeters in distance d. If the region of ten millimeters is divided into a hundred channels for example, i.e., 0.1 millimeter per one channel, the diffracted X-ray is to be detected with a positional resolution of about 0.04 degree in a range of four degrees in 2θ. It is noted that since a variation of the angle $\phi$ (i.e., variation of 2θ) is not proportional to a variation of s on the detective plane, a characteristic curve of a variation of s to a variation of $\phi$ should be prepared based on equation (20) in FIG. 8, so that it is determined what channel of the detector receives what angle range in $\phi$ of an X-ray.

TABLE 3

| $\phi$ (°) | 2 | 1 | 0.5 | 0.1 | 0.05 |
|---|---|---|---|---|---|
| s (mm) | 4.28 | 2.37 | 1.25 | 0.259 | 0.130 |
| $\phi$ (°) | 0.04 | 0.03 | 0.02 | 0.01 | |
| s (mm) | 0.104 | 0.078 | 0.052 | 0.026 | |
| $\phi$ (°) | −0.01 | −0.02 | −0.03 | −0.04 | −0.05 |
| s (mm) | 0.026 | 0.053 | 0.079 | 0.105 | 0.132 |
| $\phi$ (°) | −0.1 | −0.5 | −1 | −2 | |
| s (mm) | 0.264 | 1.37 | 2.88 | 6.29 | |

As seen from FIG. 8, if the reflective surface of the mirror is formed based on one equiangular spiral, plural different diffracted X-rays having different diffraction angles can be detected distinctly and simultaneously via the mirror with keeping the one-dimensional position-sensitive X-ray detector 20 stationary. Thus, since different diffracted X-rays having different diffraction angles can be detected simultaneously, an X-ray detection intensity can be increased as compared to the case that only a diffracted X-ray having a single diffraction angle is detected at once with the use of the conventional analyzer crystal. Therefore, the mirror enables comparatively short-time diffraction pattern measurement even using the analyzer crystal. It is noted however that when the X-ray detector is kept stationary during measurement, a coverage angle is limited to a range of about four degrees in 2θ for example. Therefore, in order to obtain the powder diffraction pattern over a wider angular range, the receiving optical system 30 should be rotated as shown in FIG. 4.

Figure 9:
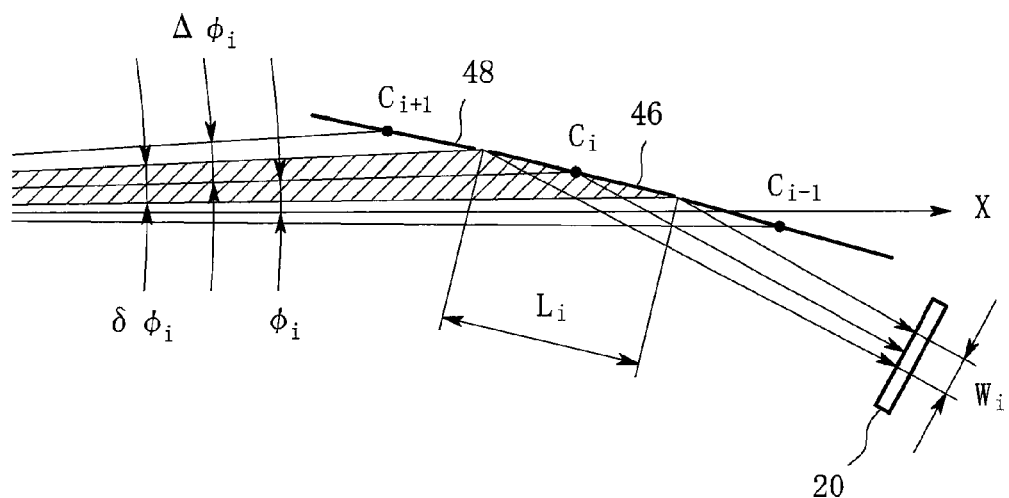
FIG. 9 shows an explanatory illustration of a mirror consisting of plural flat reflective surfaces and shows concerned mathematical equations.

Next, there will be described the procedure for making the plural flat reflective surfaces by dividing one curved reflective surface. FIG. 9 shows only three flat reflective surfaces of the mirror that consists of a combination of plural flat reflective surfaces. The centers of all the flat reflective surfaces are located on the above-described equiangular spiral. A tangential line of the equiangular spiral at an assumed center of each flat reflective surface becomes the flat reflective surface itself. Taking an i-th flat reflective surface 46 for example, the center (point $C_i$) of the flat reflective surface 46 is at an angle $\phi_i$ to the x-axis. The length of the flat reflective surface 46 is $L_i$. An angular range of the diffracted X-ray captured by the flat reflective surface 46 is $\delta\phi_i$. An angle between a diffracted X-ray travelling toward the center (point $C_i$) of the flat reflective surface 46 and a diffracted X-ray travelling toward the center (point $C_{i+1}$) of the adjacent flat reflective surface 48 is $\Delta\phi_i$. A detection width with which the reflected X-ray that has been reflected at the flat reflective surface 46 impinges on the detective plane of the X-ray detector 20 is $W_i$.

A straight line equation of the i-th flat reflective surface 46 is expressed by equation (21) in FIG. 9. A symbol $A_i$ is defined by equation (22).

A method for dividing the equiangular spiral may use various setting conditions. Table 4 shown below indicates three conditions. The first condition is that the capture angular ranges $\delta\phi$ of the respective flat reflective surfaces are equal to one another. In this case, the mirror lengths L are different from one another, and also the detection widths W assigned to the respective flat reflective surfaces are different from one another. The second condition is that the mirror lengths L of the respective flat reflective surfaces are equal to one another. In this case, the capture angular ranges δφ of the respective flat reflective surfaces are different from one another, and also the detection widths W assigned to the respective flat reflective surfaces are different from one another. The third condition is that the detection widths W assigned to the respective flat reflective surfaces are equal to one another. In this case, the capture angular ranges δφ of the respective flat reflective surfaces are different from one another, and also the mirror lengths L are different from one another.

TABLE 4

|  | Angular range | Mirror length | Detection width |
|---|---|---|---|
| First condition | $\delta\phi_1 = \delta\phi_2 = \ldots = \delta\phi_N = \delta\phi$ | $L_1 > L_2 > \ldots > L_N$ | $W_1 > W_2 > \ldots > W_N$ |
| Second condition | $\delta\phi_1 < \delta\phi_2 < \ldots < \delta\phi_N$ | $L_1 = L_2 = \ldots = L_N = L$ | $W_1 > W_2 > \ldots > W_N$ |
| Third condition | $\delta\phi_1 < \delta\phi_2 < \ldots < \delta\phi_N$ | $L_1 < L_2 < \ldots < L_N$ | $W_1 = W_2 = \ldots = W_N = W$ |

Table 5 shown below indicates a numerical example of the mirror consisting of a combination of ten flat reflective surfaces under the above-described third condition, in which the detection widths W on the detective plane are equal to one another. The detection width W corresponding to one flat reflective surface is 1.28 millimeters. A basing point on the detective surface is now defined as a point on which reflected X-rays that have been reflected at the center of the first flat reflective surface (which is the outermost one among the ten flat reflective surfaces) will reach the detective plane. With the definition of the basing point, a distance s is defined as a distance between the basing point and a point on which reflected X-rays that have been reflected at the center of any flat reflective surface will reach the detective plane. For example, in Table 5, the distance s between the basing point and a point on which reflected X-rays that have been reflected at the center of the second reflective surface will reach the detective plane is 1.28 millimeters; and the distance s between the basing point and a point on which reflected X-rays that have been reflected at the center of the third reflective surface will reach the detective plane is 2.56 millimeters. The reflected X-rays that have been reflected at the center of each flat reflective surface reach the point Q (see FIG. 8) on the detective plane, the coordinates of the point Q being ($x_p$, $y_p$). An angle (to the x-axis) of the diffracted X-rays travelling toward the center of each flat reflective surface is 4. The numerical values in FIG. 5 are calculated under the condition that r is 200 millimeters, $\theta_0$ is 13.64 degrees, and d is 50 millimeters. An actual device based on the numerical example will be described below. The one-dimensional position-sensitive X-ray detector has 128 channels, one of which has a channel size of 0.1 millimeter. Since the 128 channels detect the reflected X-rays that have been reflected at the ten flat reflective surfaces, reflected X-rays that have been reflected at one flat reflective surface will be detected by twelve or thirteen channels.

TABLE 5

| Number | s (mm) | $x_q$ (mm) | $y_q$ (mm) | φ (°) |
|---|---|---|---|---|
| 1 | 0.0000 | 288.8772 | −45.8349 | 0.0000 |
| 2 | 1.2800 | 288.2906 | −44.6972 | −0.6681 |
| 3 | 2.5600 | 287.7039 | −43.5596 | −1.2390 |

TABLE 5-continued

| Number | s (mm) | $x_q$ (mm) | $y_q$ (mm) | φ (°) |
|---|---|---|---|---|
| 4 | 3.8400 | 287.1172 | −42.4220 | −1.7434 |
| 5 | 5.1200 | 286.5305 | −41.2844 | −2.1986 |
| 6 | 6.4000 | 285.9438 | −40.1467 | −2.6155 |
| 7 | 7.6800 | 285.3571 | −39.0091 | −3.0015 |
| 8 | 8.9600 | 284.7704 | −37.8715 | −3.3620 |
| 9 | 10.2400 | 284.1838 | −36.7338 | −3.7009 |
| 10 | 11.5200 | 283.5971 | −35.5962 | −4.0212 |

Table 6 shown below indicates a numerical example of the flat reflective surfaces when the mirror consists of a combination of ten flat reflective surfaces under the condition shown in the above-described Table 5. An angle φ is an angle at the center of each flat reflective surface. The coordinates (x, y) are shown for the center together with the both ends of each flat reflective surface. For example, as to the first flat reflective surface, x-coordinate of the center is 200.0000 millimeters and its y-coordinate is 0.0000 millimeter, x-coordinate of one end is 194.1433 millimeters and its y-coordinate is 1.4213 millimeters, and x-coordinate of the other end is 204.8831 millimeters and its y-coordinate is negative 1.1850 millimeters. The symbol L represents a length of each flat reflective surface. The symbol Δφ represents an angle between the centers of two adjacent flat reflective surfaces. The total length of the ten flat reflective surfaces is about 78 millimeters.

TABLE 6

| Number | φ (°) | Δφ (°) | x (mm) | y (mm) | L (mm) |
|---|---|---|---|---|---|
|  |  |  | 194.1433 | 1.4213 |  |
| 1 | 0.0000 |  | 200.0000 | 0.0000 | 11.0515 |
|  |  | 0.6681 | 204.8831 | −1.1850 |  |
| 2 | −0.6681 |  | 209.8306 | −2.4469 | 9.6004 |
|  |  | 0.5709 | 214.1857 | −3.5576 |  |
| 3 | −1.2390 |  | 218.5893 | −4.7277 | 8.6872 |
|  |  | 0.5044 | 222.5816 | −5.7884 |  |
| 4 | −1.7434 |  | 226.6128 | −6.8975 | 8.0420 |
|  |  | 0.4552 | 230.3355 | −7.9218 |  |
| 5 | −2.1986 |  | 234.0906 | −8.9871 | 7.5538 |
|  |  | 0.4169 | 237.6025 | −9.9835 |  |
| 6 | −2.6155 |  | 241.1422 | −11.0156 | 7.1673 |
|  |  | 0.3860 | 244.4832 | −11.9898 |  |
| 7 | −3.0015 |  | 247.8486 | −12.9957 | 6.8522 |
|  |  | 0.3605 | 251.0484 | −13.9521 |  |
| 8 | −3.3620 |  | 254.2699 | −14.9372 | 6.5891 |
|  |  | 0.3389 | 257.3495 | −15.8789 |  |
| 9 | −3.7009 |  | 260.4486 | −16.8466 | 6.3640 |
|  |  | 0.3203 | 263.4242 | −17.7757 |  |
| 10 | −4.0212 |  | 266.4175 | −18.7288 | 6.1688 |
|  |  |  | 269.3023 | −19.6473 |  |
| Total |  |  |  |  | 78.0763 |

The mirror consisting of a combination of plural flat reflective surfaces has an advantage described below as compared to the curved mirror shaped in an equiangular spiral. When using the curved mirror, one channel may receive, in principle, not only a diffracted X-ray having the intended angle 2θ but also other diffracted X-rays having other angles within a small angular range unless the channel width of the detector is infinitely narrowed. In contrast, when using the mirror consisting of a combination of plural flat reflective surfaces, a certain group of channels assigned to a certain flat reflective surface is to receive diffracted X-rays having the same diffraction angles, so that the resultant angular resolution is increased up to the angular resolution of the analyzer crystal.

Figure 10:
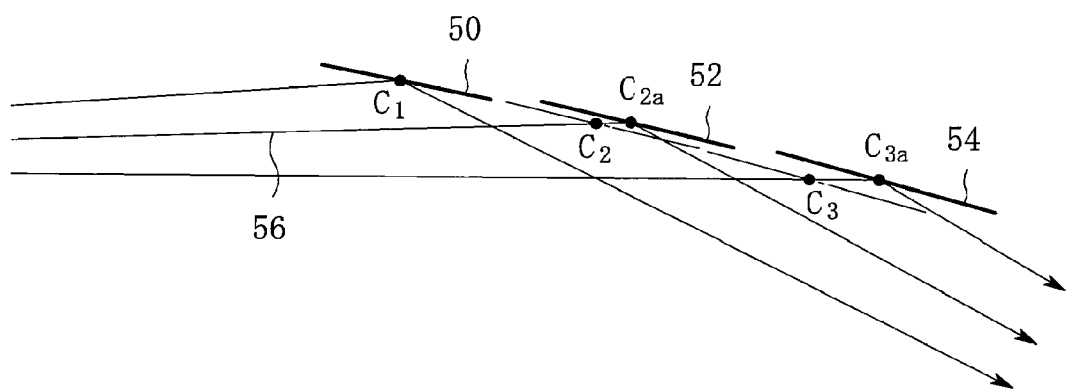
FIG. 10 shows a modification in which the centers of the flat reflective surfaces are shifted from an equiangular spiral.

Next, a modified embodiment of the mirror will be described. FIG. 10 shows a modification in which the coordinates of the centers of the respective flat reflective surfaces are shifted from an equiangular spiral. It is assumed, for example, that the centers $C_1$, $C_2$ and $C_3$ of three flat reflective surfaces 50, 52 and 54 are located on one equiangular spiral. When the central flat reflective surface 52 is slightly translated in the travelling direction of a diffracted X-ray 56, the flat reflective surface 52 is moved with keeping its slope so that its center $C_2$ is moved to $C_{2a}$. Even with the translation, an angle of the flat reflective surface 62e to the diffracted X-ray 56 is kept as it is, and therefore the diffracted X-ray 56 is reflected at the flat reflective surface 52. The right-side flat reflective surface 54 is similarly translated so that the center $C_3$ is moved to $C_{3a}$, noting that its translational distance is larger than that for the central flat reflective surface 52. Even if the plural flat reflective surfaces are shifted sequentially as mentioned above, the resultant combination mirror can properly reflect the diffracted X-rays, noting however that detection points of the reflected X-rays on the detective plane are also shifted along with the shift of the flat reflective surfaces. Accordingly, if using a large detection plane, the modification shown in FIG. 10 is preferable.

Although the above description mentions the case that the X-ray focus is the linear focus, the present invention may be applied to the point focus.

Figure 11A:
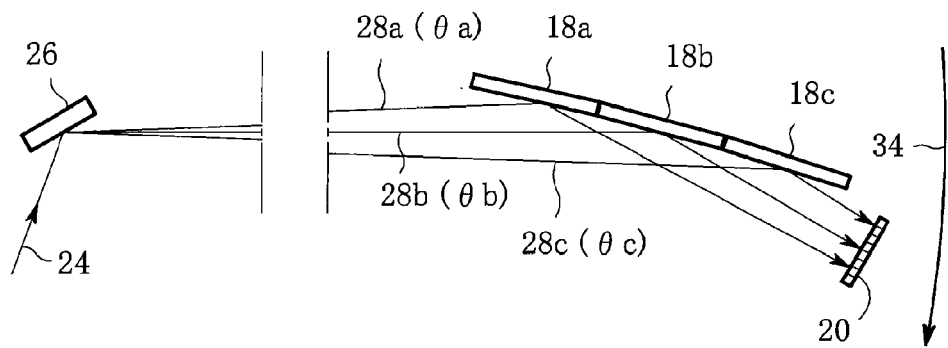
FIGS. 11A to 11C are plan views showing different states in which a diffracted X-ray beam is detected during rotation of a receiving optical system with a narrower beam width of the incident X-ray beam.
Figure 11B:
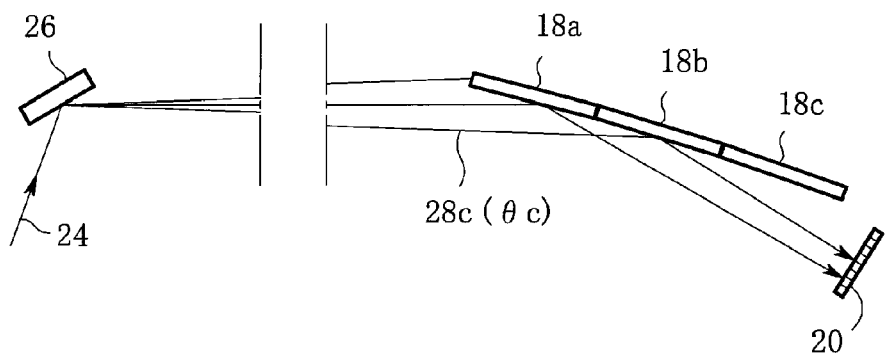
Figure 11C:
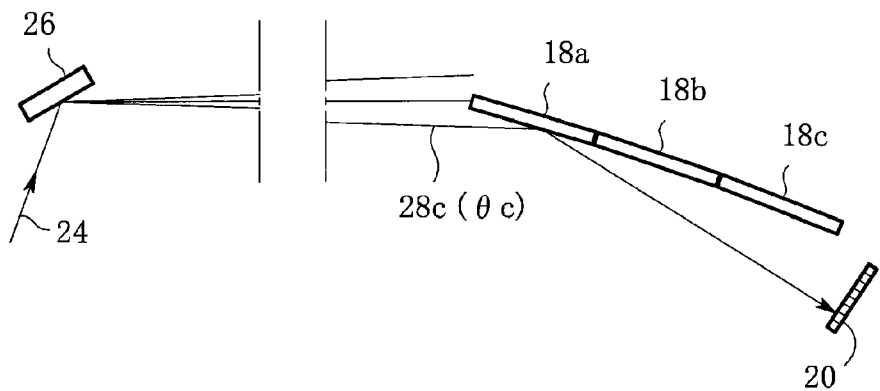

Next, there will be explained a problem in the case that the beam width of the incident X-rays is broader when the combination mirror is used. The problem is that one detection group of channels assigned to any one flat reflective surface may unfortunately receive reflected X-rays that have been reflected at the adjacent flat reflective surfaces, leading to the mixed detection. FIGS. 11A to 11C show measurement states in which diffracted X-rays are detected during rotation of the receiving optical system when the beam width of the incident X-rays is narrow, noting that the mirror is made of a combination of three partial mirrors 18a, 18b and 18c for a brief explanation. Referring to FIG. 11A, incident X-rays 24 (which form a narrow parallel X-ray beam having a beam width B) are incident on the sample 26, and diffracted X-rays 28a, 28b and 28c from the sample 26 are incident on the three partial mirrors 18a, 18b and 18c. The diffracted X-rays 28a, 28b and 28c have different Bragg angles θ, with which X-rays are diffracted at the sample 26. Namely, the diffracted X-rays 28a has the Bragg angle of θa; the diffracted X-rays 28b has the Bragg angle of θb; and the diffracted X-rays 28c has the Bragg angle of θc. Reflected X-rays that have been reflected at the three partial mirrors 18a, 18b and 18c will reach different points on the detective plane of the X-ray detector 20 respectively.

When the receiving optical system is rotated in a direction denoted by an arrow 34, the state shown in FIG. 11A alters to the state shown in FIG. 11B. Referring to FIG. 11B, the diffracted X-rays 28C having the Bragg angle θc now reach the center of the central partial mirror 18b. Namely, the state (shown in FIG. 11A) in which the diffracted X-rays 28C having the Bragg angle θc reach the center of the right side partial mirror 18c alters to the state (shown in FIG. 11B) in which the diffracted X-rays 28C reach the center of the central partial mirror 18b. As a result, although the diffracted X-rays 28c having the Bragg angle θc reach the upper right region on the detective plane of the detector 20 in the state shown in FIG. 11A, they reach the central region on the detective plane in the state shown in FIG. 11B. Thus, with the rotation of the receiving optical system, the diffracted X-rays having the same Bragg angle are detected by different regions on the detective plane.

When the receiving optical system is further rotated, the state shown in FIG. 11B alters to the state shown in 11C. Referring to FIG. 11C, the diffracted X-rays 28C having the Bragg angle θc now reach the center of the left side partial mirror 18a. As a result, the diffracted X-rays 28C having the Bragg angle θc reach the lower left region on the detective plane.

Figure 12A:
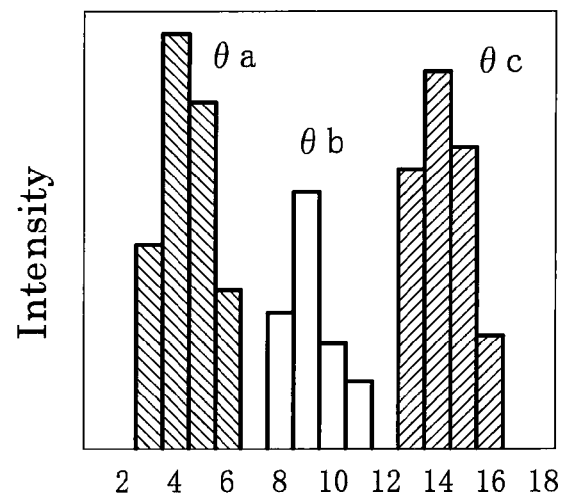
FIGS. 12A to 12C show simplified graphs showing detector outputs in the states shown in FIGS. 11A to 11C respectively.
Figure 12B:
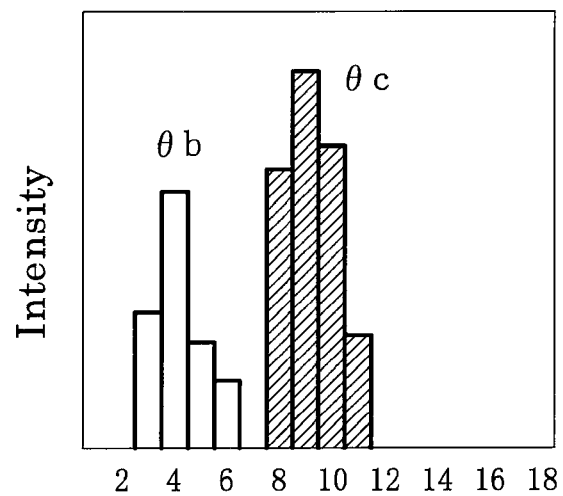
Figure 12C:
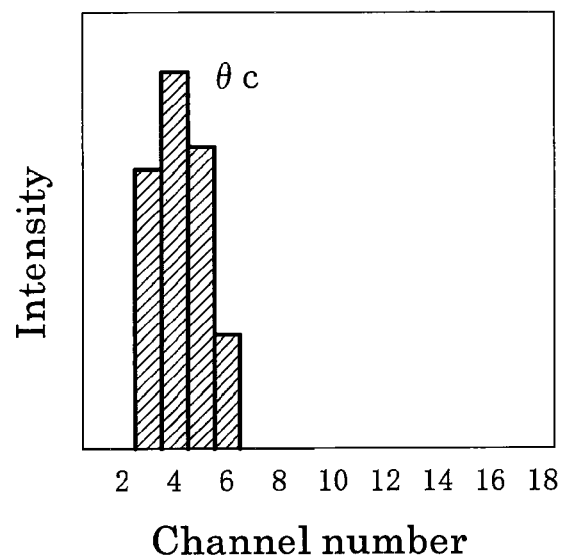

FIGS. 12A to 12C show simplified graphs showing detector outputs in the states shown in FIGS. 11A to 11C respectively. The abscissa represents the channel number of the detector, whereas the ordinate represents the X-ray intensities that were detected by the respective channels. It is assumed that the detector has eighteen channels. Since the eighteen channels receive the reflected X-rays from the three partial mirrors, one group consisting of several channels will receive the reflected X-rays from one partial mirror. The graph shown in FIG. 12A corresponds to the state shown in FIG. 11A. The channel number is defined as that the numbers 1 to 18 are assigned to the channels of the X-ray detector 20 in FIG. 11A from the lower left one to the upper right one. Referring to FIG. 12A, the diffracted X-rays 28c (which has the Bragg angle θc) coming from the partial mirror 18c are detected by several channels around the fourteenth channel, these channels being referred to as the third group of channels; the diffracted X-rays 28b (which has the Bragg angle θb) coming from the partial mirror 18b are detected by several channels around the ninth channel, these channels being referred to as the second group of channels; and the diffracted X-rays 28a (which has the Bragg angle θa) coming from the partial mirror 18a are detected by several channels around the fourth channel, these channels being referred to as the first group of channels. The X-rays detected by the third group of channels (these X-rays are detected by the thirteenth through sixteenth channels in FIG. 12A) are the diffracted X-rays 28c coming from the partial mirror 18c, and thus these X-rays all have the same Bragg angle θc (with which the X-rays are diffracted at the sample).

The graph shown in FIG. 12B corresponds to the state shown in FIG. 11B. The diffracted X-rays 28c (which has the Bragg angle θc) coming from the partial mirror 18c are now detected by the second group of channels; the diffracted X-rays 28b (which has the Bragg angle θb) coming from the partial mirror 18b are detected by the first group of channels; and the diffracted X-rays 28a (which has the Bragg angle θa) coming from the partial mirror 18a are out of the detector.

The graph shown in FIG. 12C corresponds to the state shown in FIG. 11C. The diffracted X-rays 28c (which has the Bragg angle θc) coming from the partial mirror 18c are now detected by the first group of channels; and the diffracted X-rays 28b (which has the Bragg angle θb) coming from the partial mirror 18b and the diffracted X-rays 28a (which has the Bragg angle θa) coming from the partial mirror 18a are out of the detector.

The intensity of the diffracted X-rays having the Bragg angle θc can be obtained to make a sum of the intensities on the third group of channels in the state shown in FIG. 12A, the intensities on the second group of channels in the state shown in FIG. 12B, and the intensities on the first group of channels in the state shown in FIG. 12C. In the actual measurement, the intensities detected by the respective groups of channels are recorded into a memory together with the Bragg angles during the rotation of the receiving optical system while recognizing what group of channels detects what Bragg angle X-rays.

When the diffracted X-rays 28a, 28b and 28c have narrow beam widths, different groups of channels can detect separately different diffracted X-rays having different Bragg angles, leading to no problem. However, when the diffracted X-rays 28a, 28b and 28c have broader beam widths, there is a risk in which diffracted X-rays coming from adjacent partial mirrors might be mixed each other. The risk will be explained below.

Figure 13A:
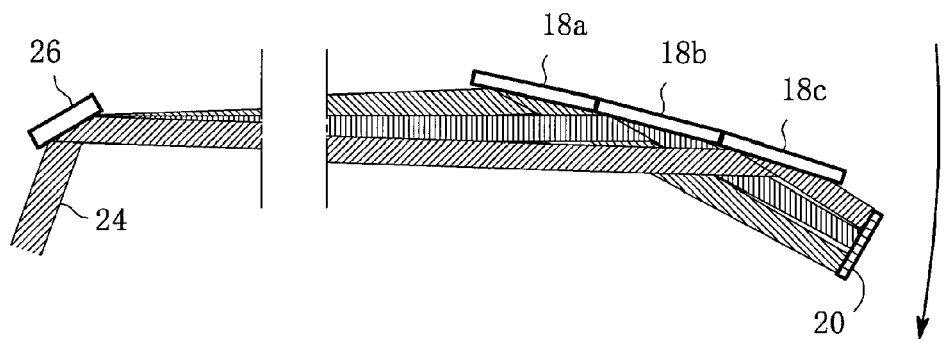
FIGS. 13A to 13C are plan views similar to FIGS. 11A to 11C but with a broader beam width of the incident X-ray beam.
Figure 13B:
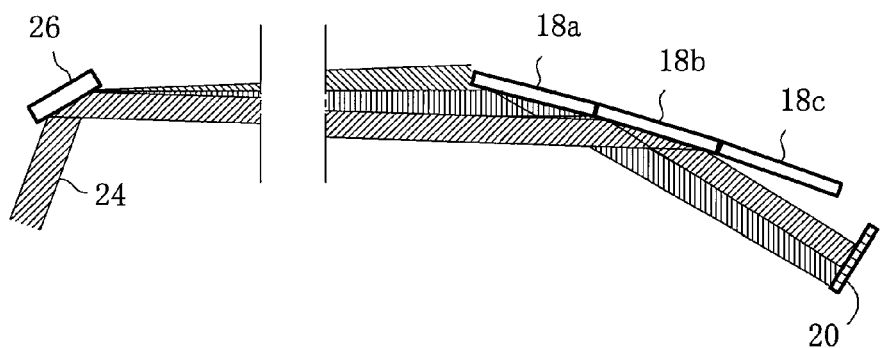
Figure 13C:
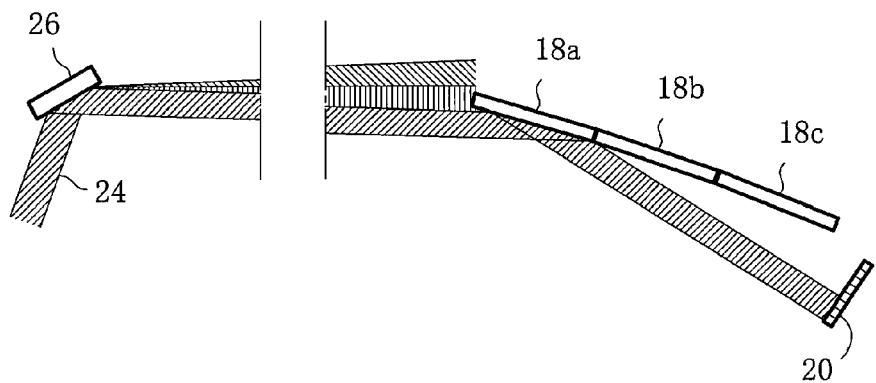
Figure 14A:
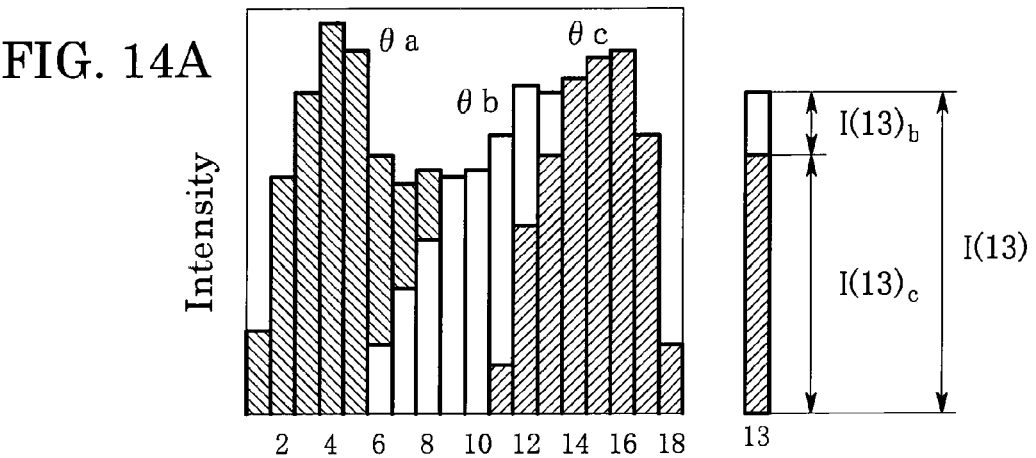
FIGS. 14A to 14C show simplified graphs indicating detector outputs in the states shown in FIGS. 13A to 13C respectively.
Figure 14B:
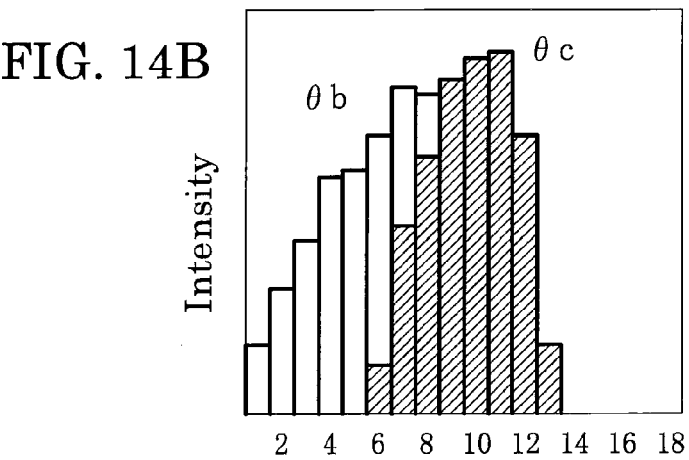
Figure 14C:
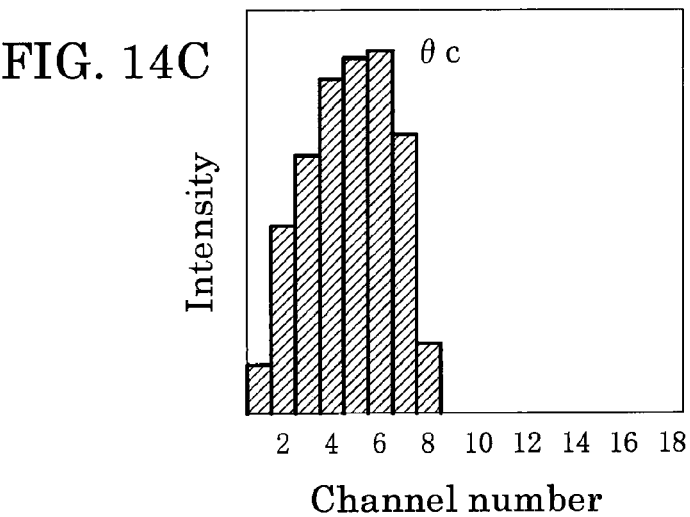

FIGS. 13A to 13C are plan views similar to FIGS. 11A to 11C but when the diffracted X-rays 28a, 28b and 28c have broader beam widths. FIGS. 14A to 14C show simplified graphs similar to FIGS. 12A to 12C but when the diffracted X-rays 28a, 28b and 28c have broader beam widths, and these graphs indicate detector outputs in the states shown in FIGS. 13A to 13C respectively. Referring to FIG. 14A, it is seen that the X-ray intensity detected by one channel may include a mixture of different X-rays having different Bragg angles especially in channels located around the boundary of the groups of channels. For example, the thirteenth channel has an X-ray intensity of I(13), which includes a mixture of the diffraction X-ray intensity $I(13)_c$ having the Bragg angle θc and the diffraction X-ray intensity $I(13)_b$ having the Bragg angle θb. Therefore, if the data processing is carried out on the assumption that the diffraction X-ray intensity detected by the thirteenth channel is concerned with the Bragg angle θc only, the resultant data would have inaccuracies. As mentioned above, when the beam widths of the diffracted X-rays are broader, there is a risk about such a problem. Even when the receiving optical system is rotated to become the state shown in FIG. 14B, there remains a risk of a mixture of the different Bragg angles. With such circumstances, the present invention can separate different Bragg angles among the detected intensities including a mixture of the different Bragg angles. Namely, the present invention can separately recognize the different Bragg angles, as described in detail below.

Figure 15:
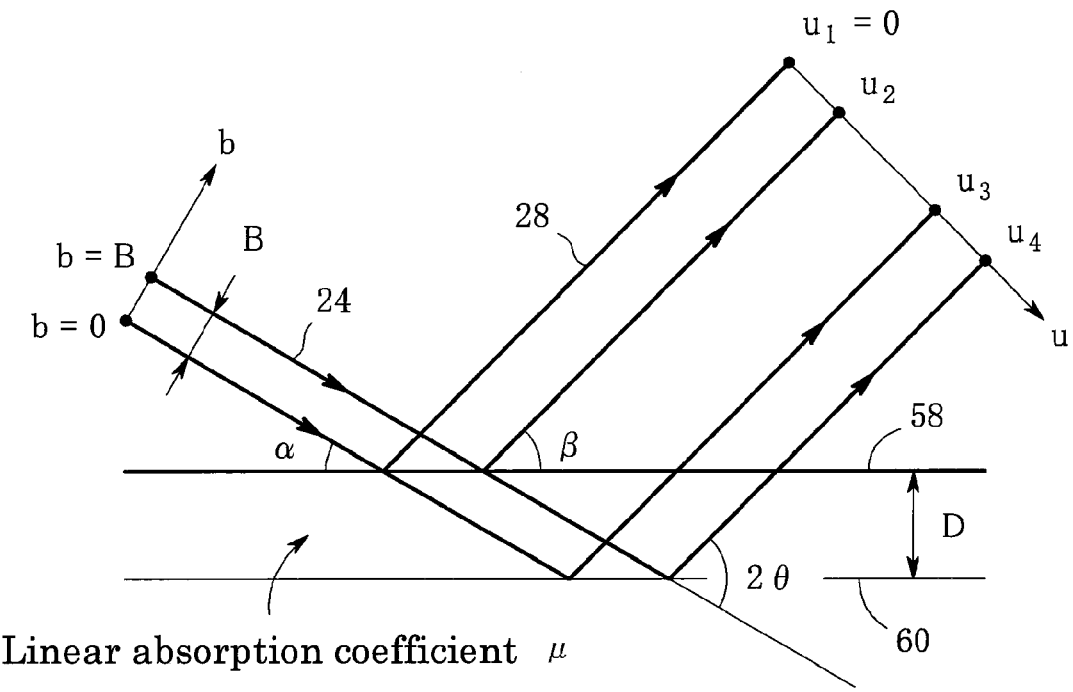
FIG. 15 is a sectional view explaining the reasons why the diffracted X-ray beam becomes broader.

The mixture problem in which one group of detective channels corresponding to any one flat reflective surface unfortunately receives diffracted X-rays coming from the adjacent flat reflective surface is caused by broadening of the diffracted X-ray beam. The broadening is caused mainly by the reasons of: (1) a broad beam width of the incident X-rays; (2) phenomena in which X-rays are diffracted also below the surface of the sample to generate a broader beam width of the diffracted X-rays; and (3) asymmetric reflection in which the outgoing angle of the diffracted X-rays from the sample surface is larger than the incident angle of the incident X-rays to the sample surface. These reasons will be explained below. FIG. 15 is a sectional view explaining the reasons. Incident X-rays 24 are incident on the sample surface 58 with an incident angle α. A beam of the incident X-rays 24 has a beam width B. Diffracted X-rays 28 that have been diffracted at the sample surface 58 with a Bragg angle θ outgo with an angle 2θ to the incident X-rays 24 and with an outgoing angle β to the sample surface 58. When the coordinate axis of a departure coordinate b is defined along a beam width of the incident X-rays 24, the value of the departure coordinate b is in a range between zero and the beam width B. When the coordinate axis of an arrival coordinate u is defined also along a beam width of the diffracted X-rays 28 (i.e., along a direction perpendicular to the diffracted X-rays 28), the value of the arrival coordinate u of the diffracted X-rays 28 is in a range between $u_1$ and $u_2$, noting that $u_1$ corresponds to the origin of the u-axis and thus is zero whereas $u_2$ is expressed by equation (23) in FIG. 15 and is equal to the beam width of the diffracted X-rays 28. Accordingly, if considering the diffraction phenomena on the sample surface 58 only, the beam width $u_2$ of the diffracted X-rays 28 would become sin β/sin α times the beam width B of the incident X-rays 24. However, if the diffraction phenomena occur also below the sample surface 58, the beam width of the diffracted X-rays 28 becomes broader. The extent of the diffraction phenomena that occur below the sample surface 58 depends on the linear absorption coefficient μ of the sample. For example, if the linear absorption coefficient is large as in the case of a metal sample, X-rays hardly enter below the sample surface, leading to less extent of the diffraction below the sample surface 58. In contrast, if the linear absorption coefficient is small as in the case of a polymer sample, X-rays easily enter below the sample surface, leading to much extent of the diffraction below the sample surface 58.

Referring to FIG. 15, the sample has a thickness D and it is assumed that the incident X-rays 24 can enter to the bottom 60 of the sample, the bottom 60 being located at a distance D from the sample surface 58, and further assumed that the X-rays are diffracted at any locations between the surface and the bottom of the sample. In this case, the beam width of the diffracted X-rays 28 becomes broader as described below. If incident X-rays having the departure coordinate b of zero are diffracted at the bottom 60, the resultant diffracted X-rays will reach a point $U_3$. If other incident X-rays having the departure coordinate b of B are diffracted at the bottom 60, the resultant diffracted X-rays will reach a point $U_4$. The coordinate of $u_3$ is expressed by equation (24) whereas the coordinate of $u_4$ is expressed by equation (25). The intensity I(u) of the diffracted X-rays at any coordinate u on the u-axis is expressed by equation (26) in FIG. 16, noting that the intensity of the incident X-rays is defined as I. Equation (26) can be transformed to equation (27), noting that fe and fs in equation (27) can be expressed by different equations depending on the range of u. The diffracted X-rays having an intensity expressed by equation (27) are further reflected at the mirror and are thereafter detected by the X-ray detector. Since the mirror has a large linear absorption coefficient, the reflection at the mirror would not affect the widthwise intensity distribution of the diffracted X-ray beam. Accordingly, it is considered that the intensity distribution expressed by equation (27) would appear as it is as the detected intensity distribution on the one-dimensional position-sensitive X-ray detector.

It is anticipated that actual calculation of intensity with the use of equation (27) would be affected by any misalignment from the design value about the relationship between the ten partial mirrors that form the mirror and the X-ray detection point. Then, the variable u is replaced with u+Δu for bringing in such misalignment as a parameter, noting that Δu is a parameter, which can be obtained by the parameter fitting operation described later.

Figure 17A:
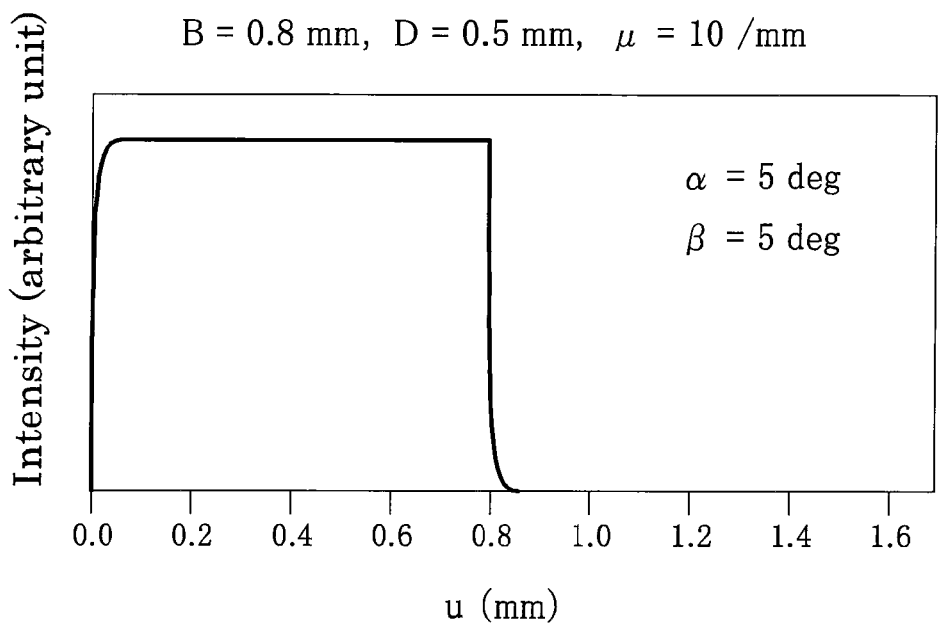
FIGS. 17A and 17B show graphs of equation (27) when the linear absorption coefficient $\mu$ is large.
Figure 17B:
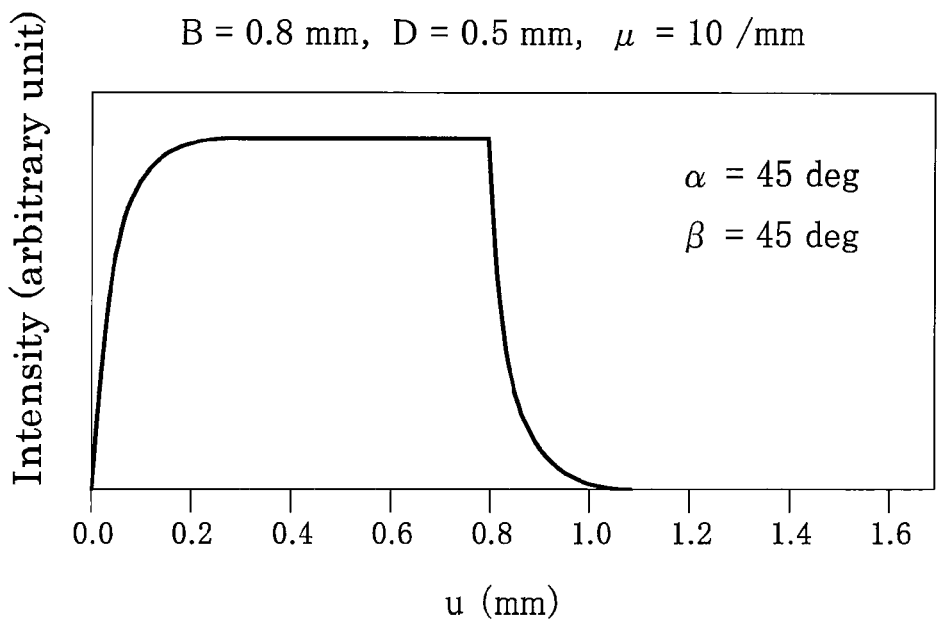

Calculation examples about the intensity distribution expressed by the above-mentioned equation (27) will be described below. FIGS. 17A and 17B show graphs of the intensity distributions when the linear absorption coefficient μ is large (10/mm). Other assumptions in calculation are that the incident X-rays have a beam width that is 0.8 millimeter and the sample has a thickness D that is 0.5 millimeter. The graph shown in FIG. 17A is for the incident angle α that is five degrees and the outgoing angle β that is five degrees. Since the linear absorption coefficient is large, the diffracted X-ray beam becomes not so broad and thus its intensity distribution shown in the graph becomes nearly a rectangle. FIG. 17B shows a graph similar to that shown in FIG. 17A but for different incident and outgoing angles, the incident angle α being 45 degrees and the outgoing angle β being 45 degrees. The intensity distribution of the diffracted X-rays in this graph spreads somewhat toward the larger side in u as compared to the graph shown in FIG. 17A that is for the small angle incidence.

Figure 18A:
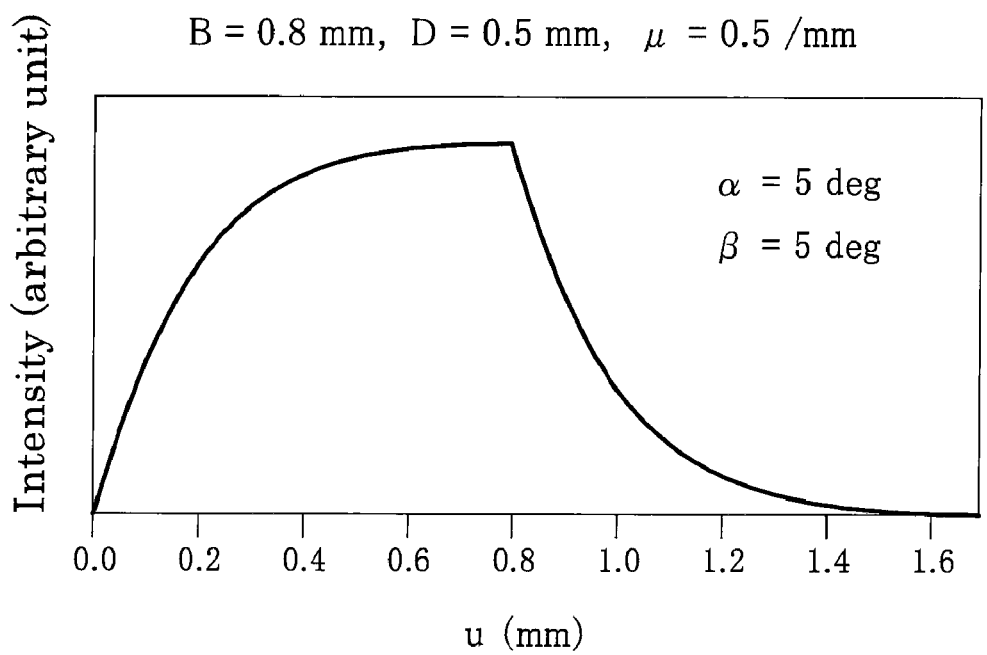
FIGS. 18A and 18B show graphs of equation (27) when the linear absorption coefficient $\mu$ is small.
Figure 18B:
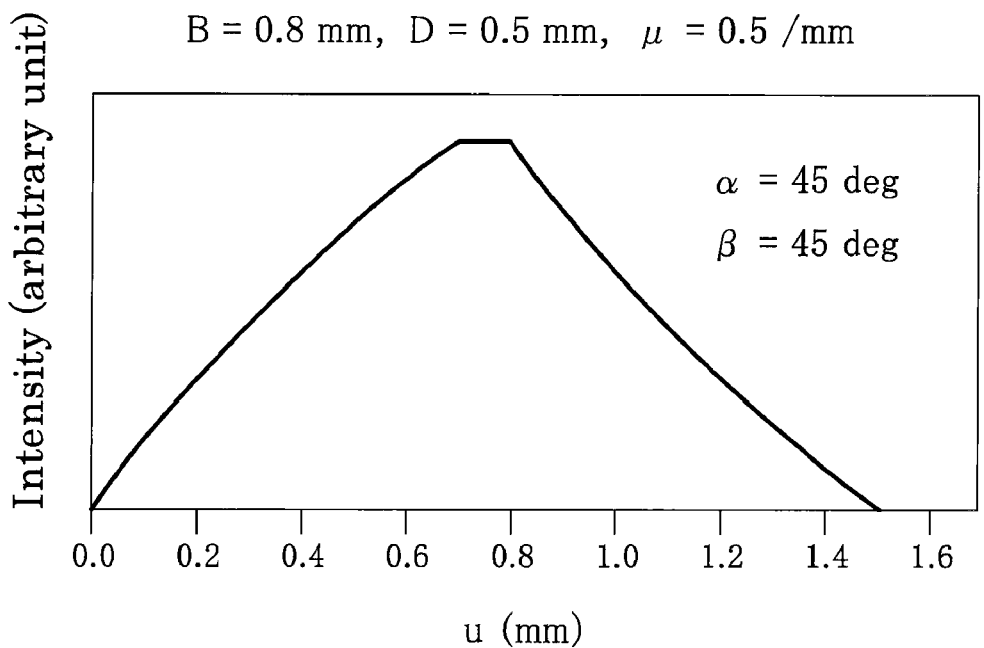

FIGS. 18A and 18B show graphs of the intensity distributions when the linear absorption coefficient μ is small (0.5/mm). The intensity distribution shown in FIG. 18A has the same assumptions as that in FIG. 17A except the linear absorption coefficient. The intensity distribution in FIG. 18A spreads toward the larger side in u as compared to that in FIG. 17A. The intensity distribution shown in FIG. 18B has the same assumptions as that in FIG. 17B except the linear absorption coefficient. The intensity distribution in FIG. 18B spreads toward the larger side in u as compared to that in FIG. 18A and also as compared to that in FIG. 17B. As mentioned above, when the linear absorption coefficient becomes smaller and when the incident and outgoing angles become larger, the intensity distribution of the diffracted X-rays is more affected by the diffracted X-rays coming from locations below the sample surface, so that the intensity distribution more spreads toward the larger side in u.

Figure 19A:
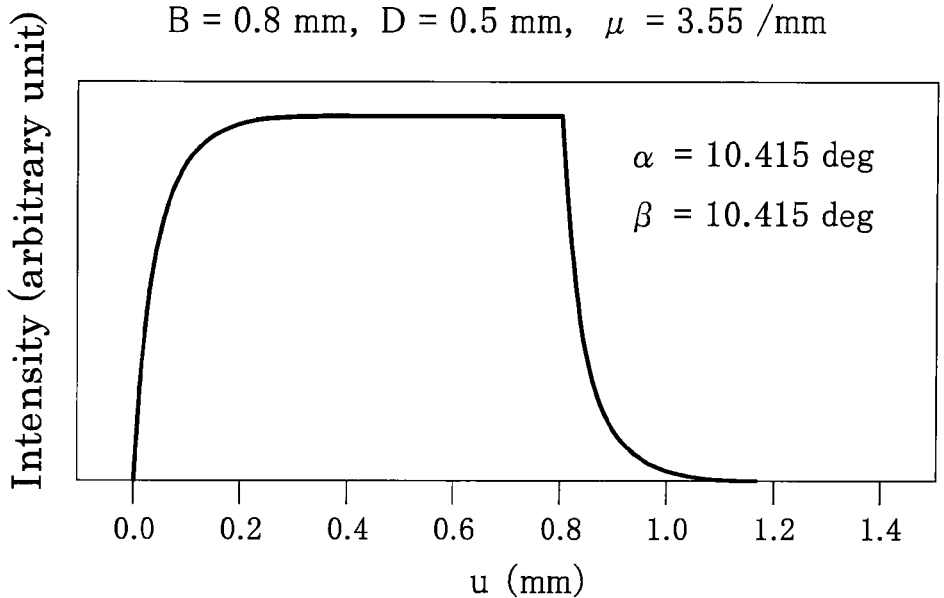
FIGS. 19A and 19B show graphs of equation (27) for an assumed actual sample.
Figure 19B:
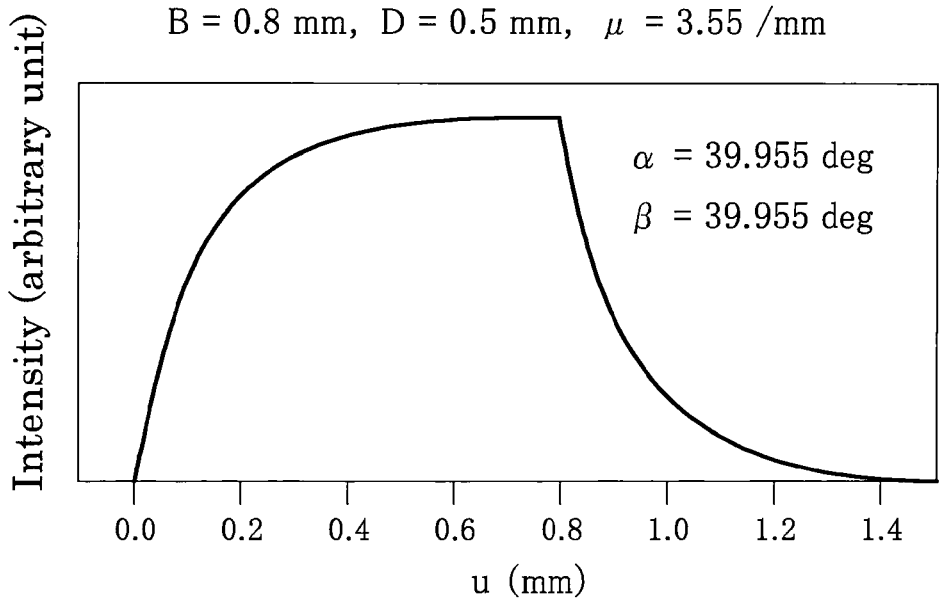

FIGS. 19A and 19B show graphs obtained by calculation for an assumed actual sample. The sample is assumed to be α-$SiO_2$ and its linear absorption coefficient μ is 3.55/mm. FIG. 19A shows an intensity distribution of the diffracted X-rays on the assumption that X-rays are diffracted at (1, −1, 0) plane of $SiO_2$; the incident angle α and the outgoing angle β are both 10.415 degrees; the incident X-ray beam has a beam width B that is 0.8 millimeter; and the sample has a thickness D that is 0.5 millimeter. FIG. 19B shows an intensity distribution of the diffracted X-rays on the assumption that X-rays are diffracted at (221) plane of $SiO_2$; the incident angle α and the outgoing angle β are both 39.955 degrees; and other assumptions are the same as those in FIG. 19A. It is seen that when the incident and outgoing angles becomes larger, the intensity distribution of the diffracted X-rays more spreads toward the larger side in u.

Figure 20:
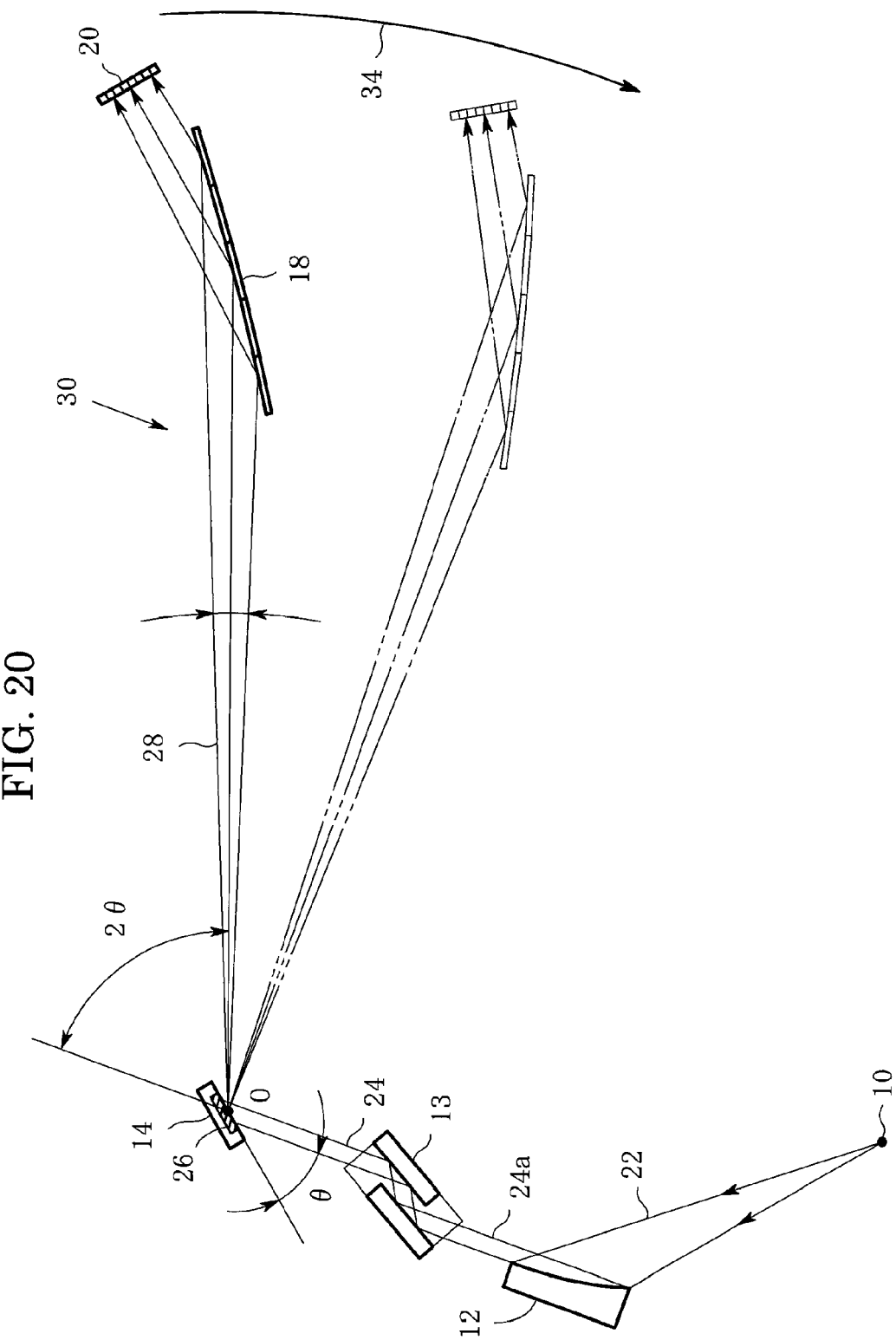
FIG. 20 is a plan view of the X-ray optical system that was actually used.
Figure 21:
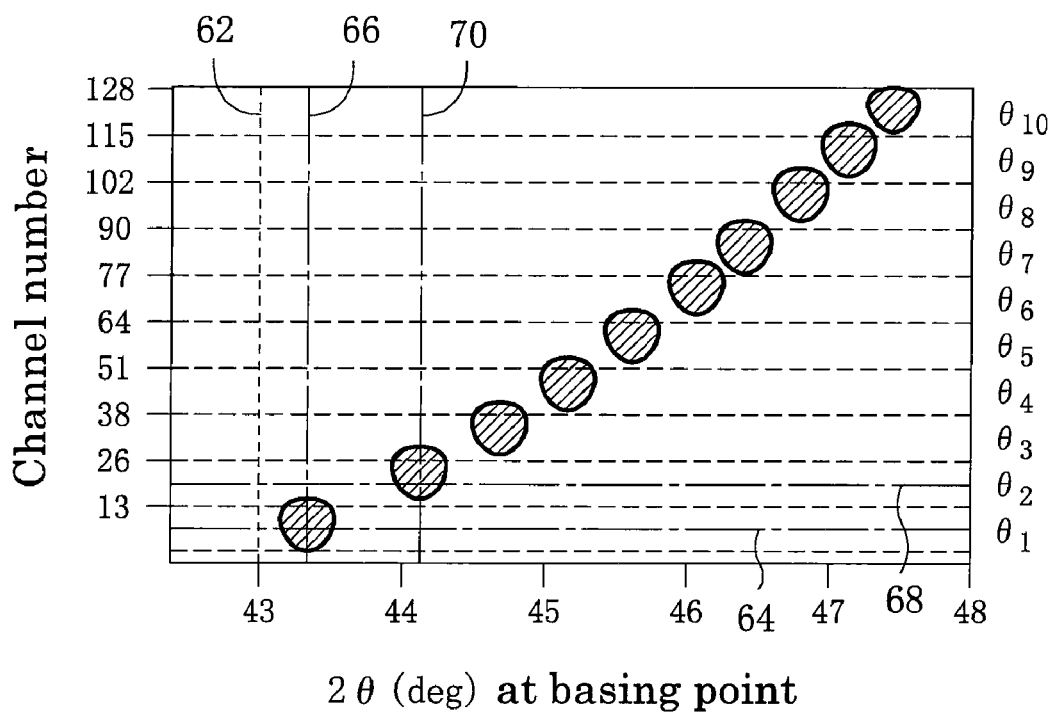
FIG. 21 shows a graph indicating a detected X-ray intensity distribution when an X-ray diffraction pattern is measured for a sample with the optical system shown in FIG. 20.

Next, there will be explained one embodiment of an operation for removing adverse effects that are caused by the mixture of different diffracted X-rays coming from adjacent flat reflective surfaces. The operation will be referred to as a corrective operation hereinafter. An X-ray optical system that was actually used is shown in FIG. 20, noting that the mirror 18 is turned over as compared to the optical system shown in FIG. 4. The mirror has the specification shown in Table 6 described above, and thus the mirror is made of a combination of the ten flat partial mirrors. FIG. 21 shows a graph indicating a detected X-ray intensity distribution when an X-ray diffraction pattern is measured for a sample 26 with the optical system shown in FIG. 20. The sample 26 is diamond powder. Since the diamond is made from carbon, its linear absorption coefficient is very small as compared to metal. Therefore, it brings much adverse affects that caused by the X-rays diffracted below the sample surface. In FIG. 21, the abscissa represents the diffraction angle 2θ whereas the ordinate represents the channel number. Areas indicated by hatching in the graph have the detected X-ray intensities higher than the predetermined level.

Attention is required in understanding the abscissa. Since the mirror is divided into the ten partial mirrors, the diffracted X-rays simultaneously detected by the X-ray detector have ten kinds of Bragg angles. It is now assumed that when the receiving optical system is located at a certain rotation angle, the diffracted X-rays that have been reflected at the first partial mirror have the Bragg angle $\theta_1$ with which the X-rays diffracted at the sample. With such assumptions, almost every the diffracted X-rays having the Bragg angle $\theta_1$ will be detected on the first to thirteenth channels (i.e., the first group of channels). In this situation, the diffracted X-rays that have been reflected at the second partial mirror have the Bragg angle $\theta_2$ and almost every those X-rays will be detected on the fourteenth to twenty-sixth channels (i.e., the second group of channels). The difference between $\theta_1$ and $\theta_2$ is 0.6681 degree, which corresponds to Δφ appearing between numbers 1 and 2 in Table 6 mentioned above. Similarly, the diffracted X-rays detected on the third to tenth groups of channels have the Bragg angles $\theta_3$ to $\theta_{10}$ respectively. Accordingly, the diffracted X-rays simultaneously detected by the X-ray detector including the 128 channels have the ten kinds of Bragg angles, and their measured data are arranged vertically in the graph shown in FIG. 21. As mentioned above, the vertically-arranged measured data (noting that only the areas having intensities higher than the predetermined level are indicated by hatching) have the ten kinds of Bragg angles. The abscissa, however, represents only one kind of 2θ. The truth is, the 2θ in abscissa represents only one kind of 2θ which corresponds to a certain point on the X-ray detector: the certain point will be referred to as a basing point hereinafter. Therefore, it should be noted that the measured data on the respective channels in the graph are to have the Bragg angles whose values are shifted from 2θ represented in abscissa by certain degrees.

The graph shown in FIG. 21 can be obtained as described below. The receiving optical system is located at a certain rotation angle so that the basing point corresponds to 2θ that is 43 degrees for example. With the arrangement, diffracted X-rays from the sample are detected, so that detected intensities are obtained from the respective 128 channels of the X-ray detector. The obtained data are recorded into a memory and are indicated as the measured data that are on a vertical line 62 in FIG. 21. It should be noted again that only the data having intensities higher than the predetermined level are indicated by hatching in the graph. Next, the receiving optical system is rotated by a predetermined small angle and thereafter the diffracted X-rays are detected by the X-ray detector and recorded. Those data are indicated vertically on the immediate right of the vertical line 62 in FIG. 21. Repeating these operations, the measured data can be obtained in a range of five degrees (between 43 to 48 degrees) in 2θ with an interval of 0.01 degree for example. Since the number of pieces of 2θ is 500 and the channel number is 128, the number of data that should be recorded becomes 64000, which is obtained by 500 times 128. After completion of recording these data, the corrective operation for the data will be carried out.

Figure 22:
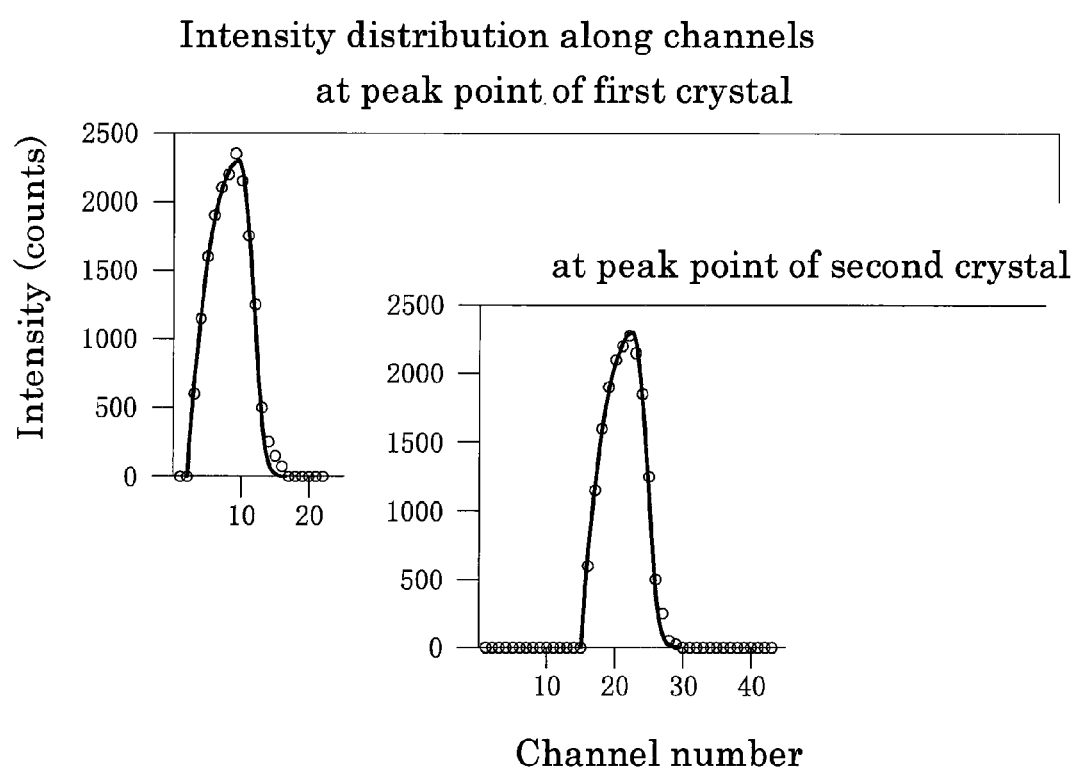
FIG. 22 shows graphs indicating diffracted X-ray intensity distributions along channels.

The seventh channel is selected as an almost central channel of the first group of channels, and an intensity distribution depending on 2θ is made based on the measured data on the seventh channel. This step means that an intensity distribution is made based on the measured data on a horizontal line 64 in FIG. 21. The intensity distribution is an ordinary diffraction profile. A point with the maximum intensity is searched in the diffraction profile. In the graph shown in FIG. 21, the maximum intensity point on the horizontal line 64 is located at about 43.7 degrees in 2θ of the basing point. Next, on the vertical line with 2θ that represents the maximum intensity point, measured data that have been simultaneously obtained on other channels are collected and an intensity distribution along channels (i.e., an intensity distribution in a direction of variation in channel number) is made. Namely, an intensity distribution of the measured data is made on a vertical line 66 in FIG. 21: this distribution will be referred to as the first along-channels distribution hereinafter. The first along-channels distribution is an intensity distribution along channels where the diffracted X-rays that have been reflected at the first partial mirror (which is also referred to as the first crystal) show the maximum intensity. Referring to FIG. 22, the first along-channels distribution is shown as a chain of white circles in a graph for the first crystal. In the graphs in FIG. 22, the abscissa represents the channel number whereas the ordinate represents X-ray intensities that were detected on the respective channels. The white circles represent the measured data. Solid lines will be explained later.

Referring back to FIG. 21, like the first group of channels, the twentieth channel is selected as an almost central channel of the second group of channels, and an intensity distribution depending on 2θ is made based on the measured data on the twentieth channel. This step means that an intensity distribution is made based on the measured data on a horizontal line 68 in FIG. 21. A point with the maximum intensity is searched in the diffraction profile. In the graph shown in FIG. 21, the maximum intensity point on the horizontal line 68 is located at about 44.2 degrees in 2θ of the basing point. Next, on the vertical line with 2θ that represents the maximum intensity point, measured data that have been simultaneously obtained on other channels are collected and an intensity distribution along channels is made. Namely, an intensity distribution of the measured data is made on a vertical line 70 in FIG. 21: this distribution will be referred to as the second along-channels distribution hereinafter. The second along-channels distribution is an intensity distribution along channels where the diffracted X-rays that have been reflected at the second partial mirror (which is also referred to as the second crystal) show the maximum intensity. In FIG. 22, the second along-channels distribution is shown as a chain of white circles in another graph for the second crystal. Repeating similar operations for the third to the tenth groups of channels, the third to the tenth along-channels distributions can be obtained.

Considering the first along-channels distribution, there is the possibility that the distribution data may include not only the diffracted X-rays (which have a Bragg angle of $\theta_1$ for example) that have been reflected at the first partial mirror but also the diffracted X-rays that have been reflected at the second to the tenth partial mirrors. Then, assuming that the first along-channels distribution is made of, in principle, a combination of intensities of the diffracted X-rays that have been reflected at all the ten partial mirrors, the corrective operation described below is carried out.

When assuming that the first along-channels distribution is made of a combination of intensities of the diffracted X-rays that have been reflected at the ten partial mirrors, an along-channels distribution of the diffracted X-rays that have been reflected at only one partial mirror is assumed to be expressed by equation (27) in FIG. 16. Determination of the along-channels distribution of the diffracted X-ray intensity based of equation (27) requires respective values of an X-ray intensity I, an incident angle α, an outgoing angle β, a linear absorption coefficient μ, a beam width B of the incident X-rays, and a thickness D of the sample. Of these values, the incident angle α and the outgoing angle β have been determined in the measurement. The remaining parameters, i.e., I, μ, B and D, are to be determined by a parameter fitting operation with the least squares method so that the actual measured data are consistent with the theoretical values as well as possible. Since the first along-channels distribution is assumed to be a combination of intensities of the diffracted X-rays that have been reflected at the ten partial mirrors, it is necessary to calculate respective intensities of the diffracted X-rays that have been reflected at the respective partial mirrors. Calculation of the diffracted X-ray intensity coming from the first partial mirror requires an incident X-ray intensity $I_{1,1}$ to the first partial mirror. The first suffix 1 belonging to I represents that the intensity relates to the first along-channels distribution, whereas the second suffix 1 belonging to I represents that the intensity is for calculating the diffracted X-ray intensity from the first partial mirror. In addition, when calculating the diffracted X-ray intensity coming from the first partial mirror, the variable u is replaced with u+Δu in consideration of the above-mentioned misalignment from the design value. Accordingly, calculation of the diffracted X-ray intensity coming from the first partial mirror requires, as parameters, $I_{1,1}$, $\Delta u_1$, μ, B and D.

Similarly, calculation of the diffracted X-ray intensity coming from the second partial mirror requires, as parameters, $I_{1,2}$, $\Delta u_2$, μ, B and D, and so on. Then, calculation of the first along-channels distribution requires the calculation of the diffracted X-ray intensities coming from the first to the tenth partial mirrors, the latter requiring, as parameters, $I_{1,1}$ to $I_{1,10}$, $\Delta u_1$ to $\Delta u_{10}$, μ, B and D. Calculation of the second along-channels distribution requires the calculation of the diffracted X-ray intensities coming from the first to the tenth partial mirrors, the latter requiring, as parameters, $I_{2,1}$ to $I_{2,10}$, $\Delta u_1$ to $\Delta u_{10}$, μ, B and D, and so on. After all, calculation of the first to the tenth along-channels distributions requires, as parameters, $I_{1,1}$ to $I_{10,10}$, $\Delta u_1$ to $\Delta u_{10}$, μ, B and D. The total number of pieces of the required parameters is 113, which includes $I_{1,1}$ to $I_{10,10}$ (a hundred in number of pieces), $\Delta u_1$ to $\Delta_{10}$ (ten in number of pieces), μ, B and D. In contrast, the total number of pieces of the measured data is as follows: the number of pieces of 2θ is 500 on the assumption that the measurement is carried out in a range of five degrees (between 43 to 48 degrees) in 2θ with an interval of 0.01 degree for example; the channel number is 128; and therefore the total number of pieces of measured data that should be recorded into a memory becomes 64000, which is 500 times 128. The broader in the angular range the measurement is carried out, the more in number the total number of pieces of the measured data is. It is noted that the angular interval in 2θ is about 0.002 to 0.02 degree in the ordinary diffraction measurement. Incidentally, among the many measured data mentioned above, there are used, for the parameter fitting operation with the above mentioned 113 parameters, only the measured data on the first to the tenth along-channels distribution (1280 in number of pieces, which is 128 times 10) at respective certain measurement locations. The 113 parameters are determined with the least squares method so that the measured data are consistent with the theoretical, calculated diffracted X-ray intensities as well as possible. The solid line in the graph for the first crystal in FIG. 22 is the resultant along-channel distribution that has been obtained with the parameter fitting operation for the first partial mirror (i.e., the first crystal). The solid line in the graph for the second crystal in FIG. 22 is similar to that for the first crystal. It is noted that it is preferable to use suitable initial values in the parameter fitting operation. For example, in this embodiment, the initial values are as follows: D is 0.35 millimeter; μ is 0.5/mm; and B is 0.8 millimeter.

Now, the 113 parameters have been determined. Next, there should be determined how much each measured data includes different diffracted X-ray intensities that have been reflected at different partial mirrors with the use of the determined parameters $\Delta u_1$ to $\Delta u_{10}$, μ, B and D. For such a determination process, the measured values on the along-channels distributions are selected at any value in 2θ of the basing point, on the other hand theoretical diffracted X-ray intensities coming from the ten partial mirrors are calculated with the use of the determined parameters $\Delta u_1$ to $\Delta u_{10}$, μ, B and D and also unknown ten X-ray intensities $I_1$ to $I_{10}$. The intensities $I_1$ to $I_{10}$ are specific to their 2θ positions, and are used for X-ray intensity calculation with equation (27). As to a certain 2θ point, the number of pieces of the measured data is 128 (i.e., data for the 128 channels), whereas the number of pieces of the unknown parameters are ten, i.e., $I_1$ to $I_{10}$. Then, the parameter fitting operation can be carried out with the use of the measured data, the calculated values, and the least squares method to determine the optimum $I_1$ to $I_{10}$. With the determined $I_1$ to $I_{10}$, the diffracted X-ray intensities coming from the respective partial mirrors can be calculated for the respective channels at the certain 2θ position. In general, the detected intensity on a certain channel may be expressed by a combination of diffracted X-ray intensities coming from adjacent two partial mirrors at most. Since a sum of the two calculated intensities is, in general, not consistent with the measured intensity, the measured intensity is prorated into two intensities so as to have the same ratio as the two calculated intensities. Thus, the measured intensity on the certain channel has been divided into two diffracted X-ray intensities coming from two partial mirrors. This operation is carried out for all the measured data. As a result, there can be determined a mixture ratio of the different diffracted X-ray intensities having different Bragg angles for all the measured data. After completion of this step, the diffracted X-ray intensities having the same Bragg angle are integrated for all the measured data to obtain the diffracted X-ray intensities for the respective Bragg angles. Thus, there can be removed the adverse effects that are caused by the mixture of the diffracted X-rays coming from the adjacent partial mirrors.

Figure 23A:
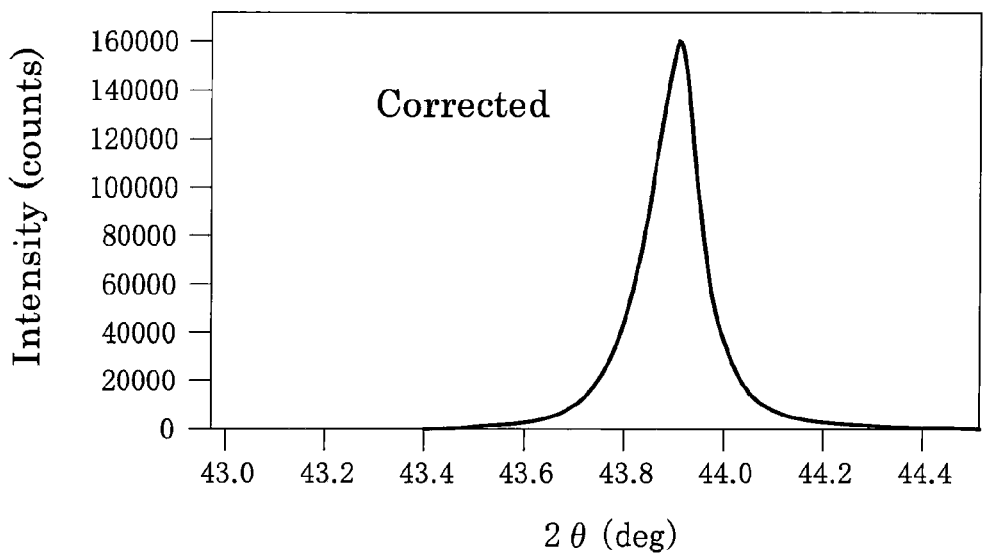
FIGS. 23A and 23B show graphs indicating advantageous effects of the corrective operation.
Figure 23B:
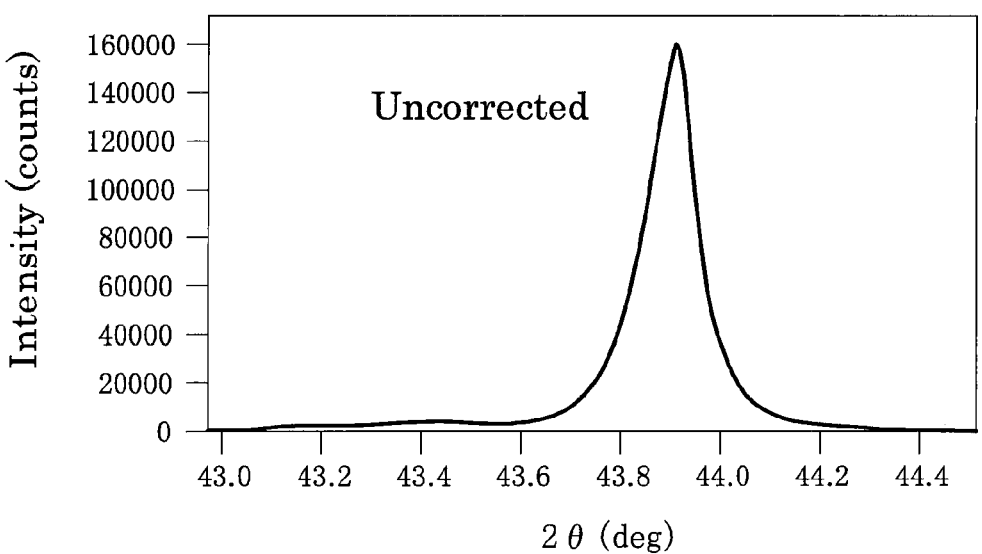

FIGS. 23A and 23B show graphs indicating advantageous effects of the corrective operation mentioned above. A graph shown in FIG. 23A indicates a diffraction profile that has been corrected. A graph shown in FIG. 23B indicates a diffraction profile that has been uncorrected. It is seen that the uncorrected diffraction profile has an additional increase in intensity at the left side foot (i.e., at the lower angle side) of the diffraction peak as compared to the corrected diffraction profile. The additional increase would not exist actually and it appears under the adverse effects that are caused by the mixture of the diffracted X-rays coming from the adjacent partial mirrors. Thus, the corrective operation can remove the adverse effects.

Figure 24:
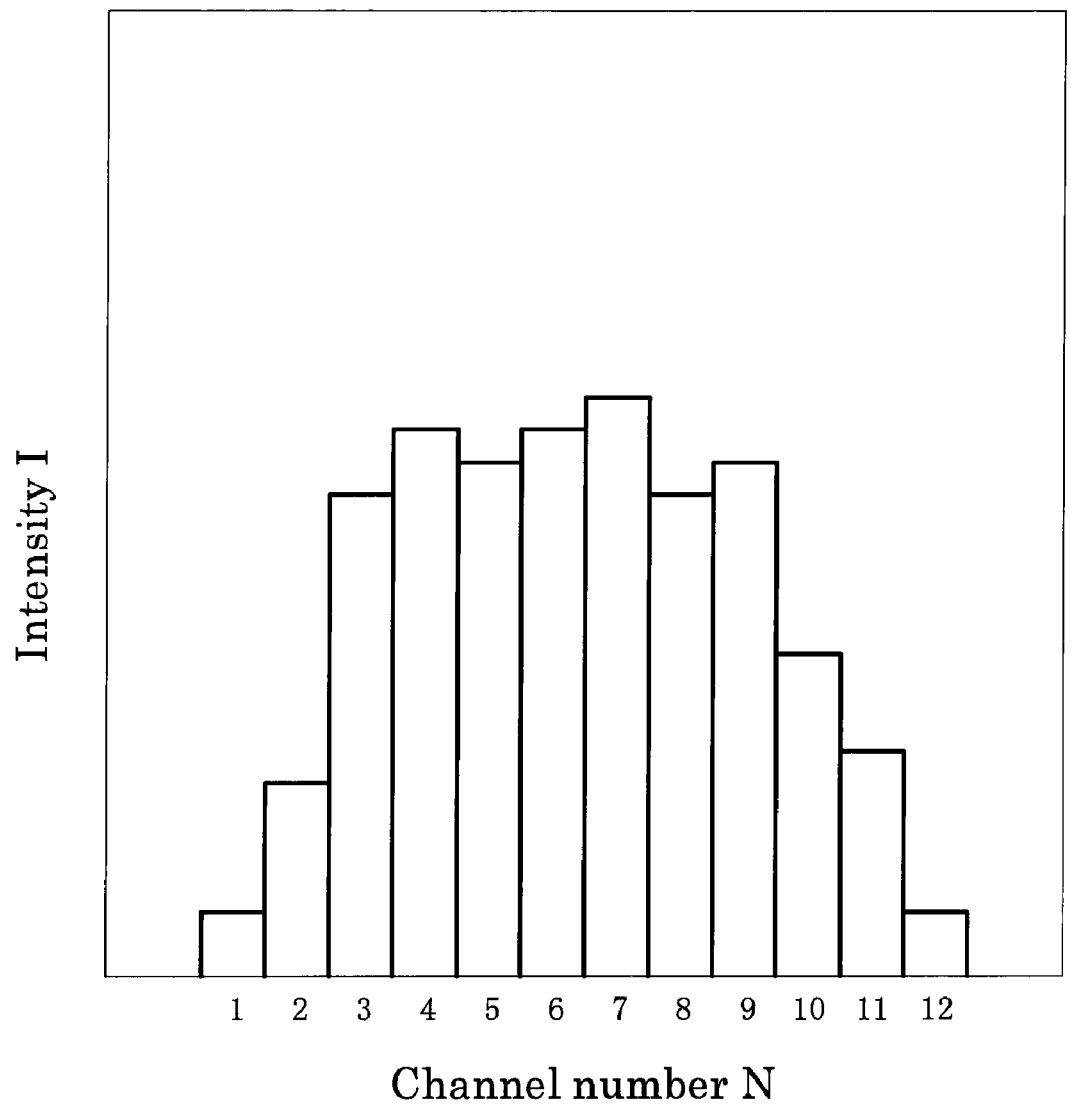
FIG. 24 shows a graph indicating one example of a detected intensity distribution along channels for the first group of channels.
Figure 25:
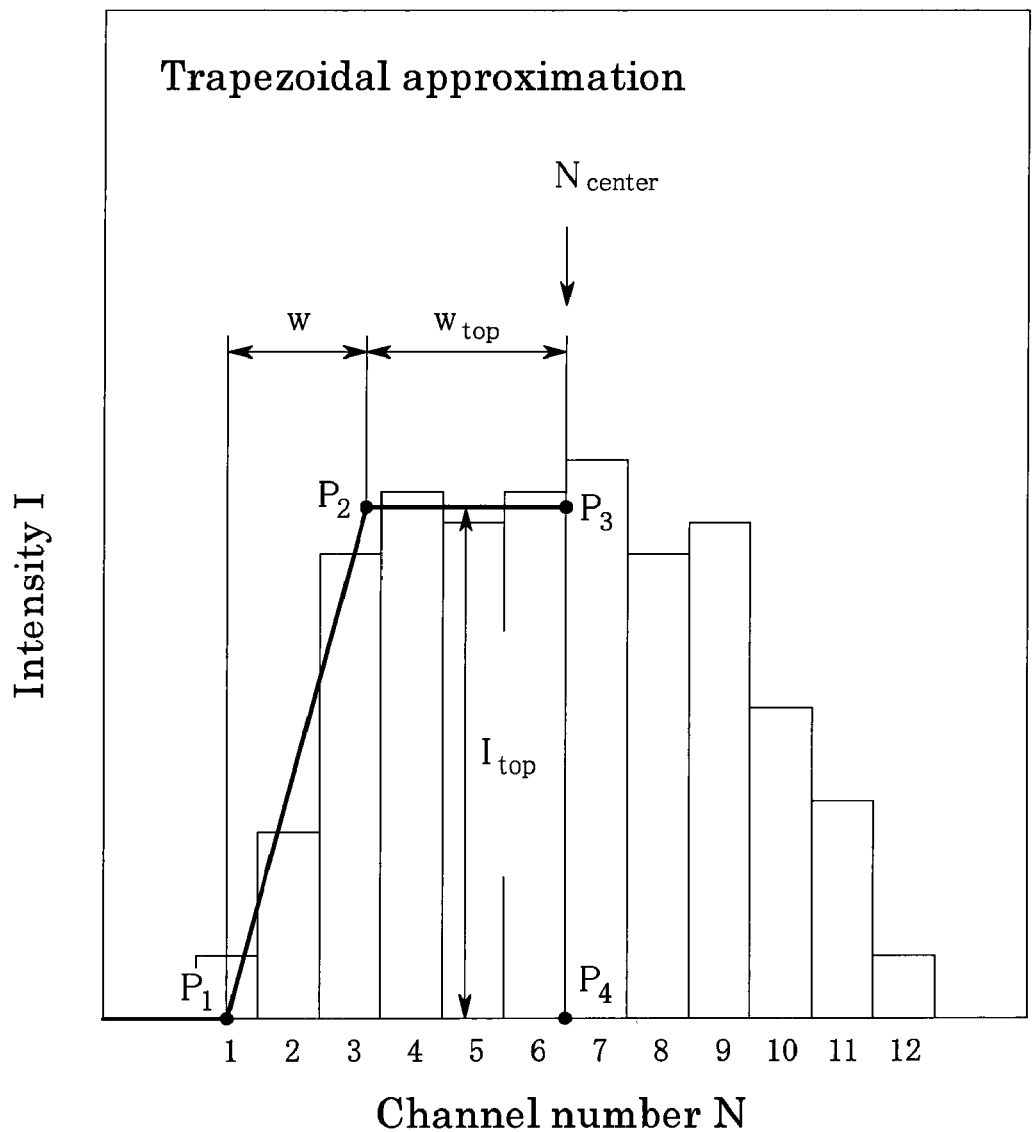
FIG. 25 shows a graph indicating a trapezoidal approximation in the left half of the distribution along channels shown in FIG. 24.

Although the above-mentioned corrective operation is based on the along-channels distribution that is expressed by equation (27) in FIG. 16, another corrective operation may be carried out as will be described below. FIG. 24 shows a graph indicating one example of a detected intensity distribution along channels for the first group of channels, the first group being located at the outermost position of the X-ray detector and including the first to twelfth channels. The graph indicates the diffracted X-ray intensities coming from the first partial mirror (i.e., the first crystal). FIG. 25 shows a graph indicating a trapezoidal approximation in the left half of the along-channels distribution shown in FIG. 24. Since the left half for the first crystal would have no risk of including interfusion of the diffracted X-rays coming from the adjacent crystal, the left half for the first crystal is suitable for making an approximation of the left half shape of the along-channels distribution under the condition of including no interfusion of the diffracted X-rays coming from the adjacent crystal. The trapezoid is made of a connection of the four vertices $P_1$ to $P_4$. The X-ray intensity is constant from the center $N_{center}$ of the first group of channels to a point away leftward from the center by a distance $w_{top}$ (i.e., from the point $P_3$ to the point $P_2$): its intensity I(N) is expressed by equation (28) in FIG. 27. In equation (28), BG is an intensity of the background, and $I_{top}$ is an intensity on the top base of the trapezoidal approximation. The X-ray intensity slopes down from the point $P_2$ to the point $P_1$: its intensity I(N) is expressed by equation (29) in FIG. 27. The X-ray intensity where the channel number is smaller than the point $P_1$ is expressed by equation (30) in FIG. 27: its intensity includes only the background intensity BG. Parameters which should be determined in the trapezoidal approximation are BG, $I_{top}$, $w_{top}$, and w (see FIG. 25).

Figure 26:
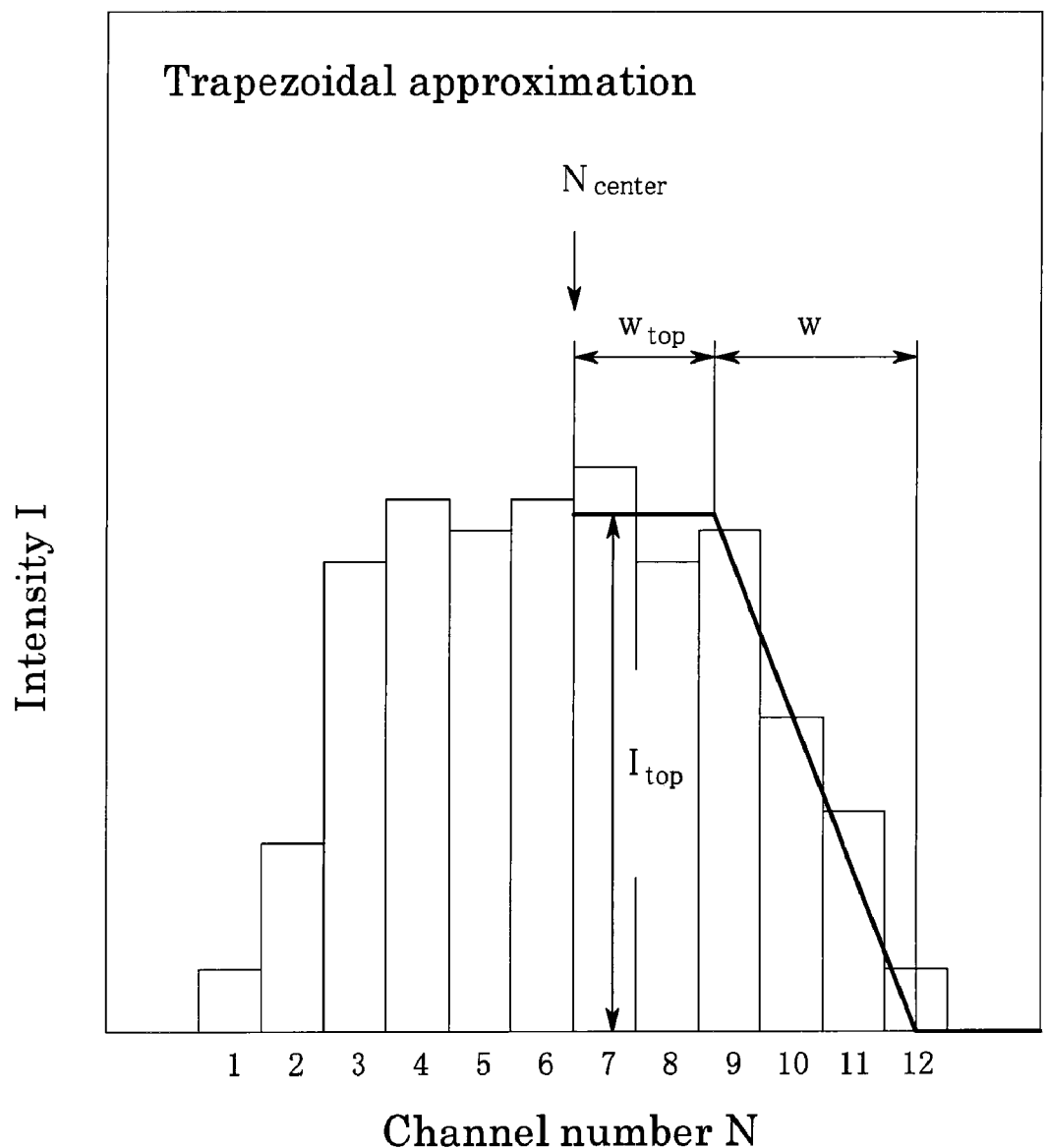
FIG. 26 shows a graph indicating a trapezoidal approximation in the right half of a detected intensity distribution along channels for the tenth group of channels.

FIG. 26 shows a graph indicating a trapezoidal approximation in the right half of the along-channels distribution of a detected intensity for the tenth group of channels, which is located at the opposite end of the X-ray detector. The graph indicates the diffracted X-ray intensities coming from the tenth partial mirror (i.e., the tenth crystal). The graph indicates a trapezoidal approximation in the right half of the along-channels distribution. Since the right half for the tenth crystal would have no risk of including interfusion of the diffracted X-rays coming from the adjacent crystal, the right half for the tenth crystal is suitable for making an approximation of the right half shape of the along-channels distribution under the condition of including no interfusion of the diffracted X-rays coming from the adjacent crystal. The X-ray intensity in the trapezoidal approximation is expressed by equations (31) to (33) in FIG. 27 as is the case with the left half of the first group of channels.

Figure 28:
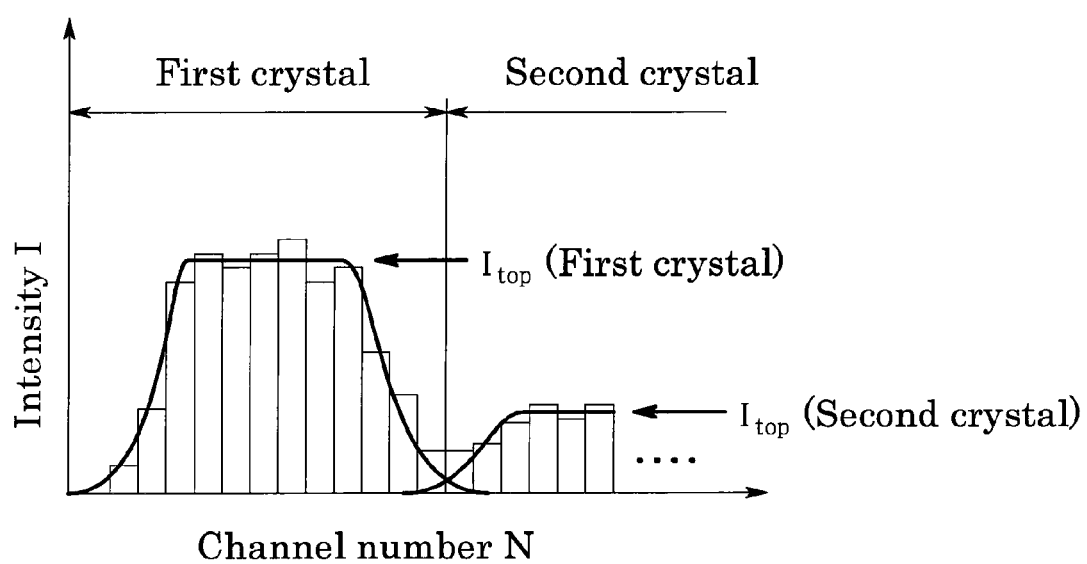
FIG. 28 shows a graph for explaining a parameter fitting operation.

Then, the parameter fitting operation is carried out with the least squares method so that the X-ray intensities expressed by the equations in FIG. 27 are consistent with the measured X-ray intensities shown in FIGS. 25 and 26 as well as possible. As a result, there can be obtained the four parameters BG, $I_{top}$, $w_{top}$, and w relating to the trapezoidal approximation of the left half of the along-channels distribution, and the other four parameters BG, $I_{top}$, $w_{top}$, and w relating to the trapezoidal approximation of the right half of the along-channels distribution. It is noted that it is preferable in the determination of the parameters to use the measured data obtained around the Bragg angle because they would have the maximum intensity. Then, with the use of these determined parameters, the parameter fitting operation is carried out as shown in FIG. 28 for the measured data of the along-channels distribution at the respective 2θ positions. The target parameters in this parameter fitting operation are the maximum intensities $I_{top}$ of the diffracted X-rays coming from the respective partial mirrors (crystals). The right foot of the along-channels distribution of the diffracted X-rays coming from the first crystal may overlap on the left foot of the along-channels distribution of the diffracted X-rays coming from the second crystal. In such a case, the measured intensity may be prorated into two intensities for any channel so as to have the same ratio as the two calculated intensities.

Figure 29:
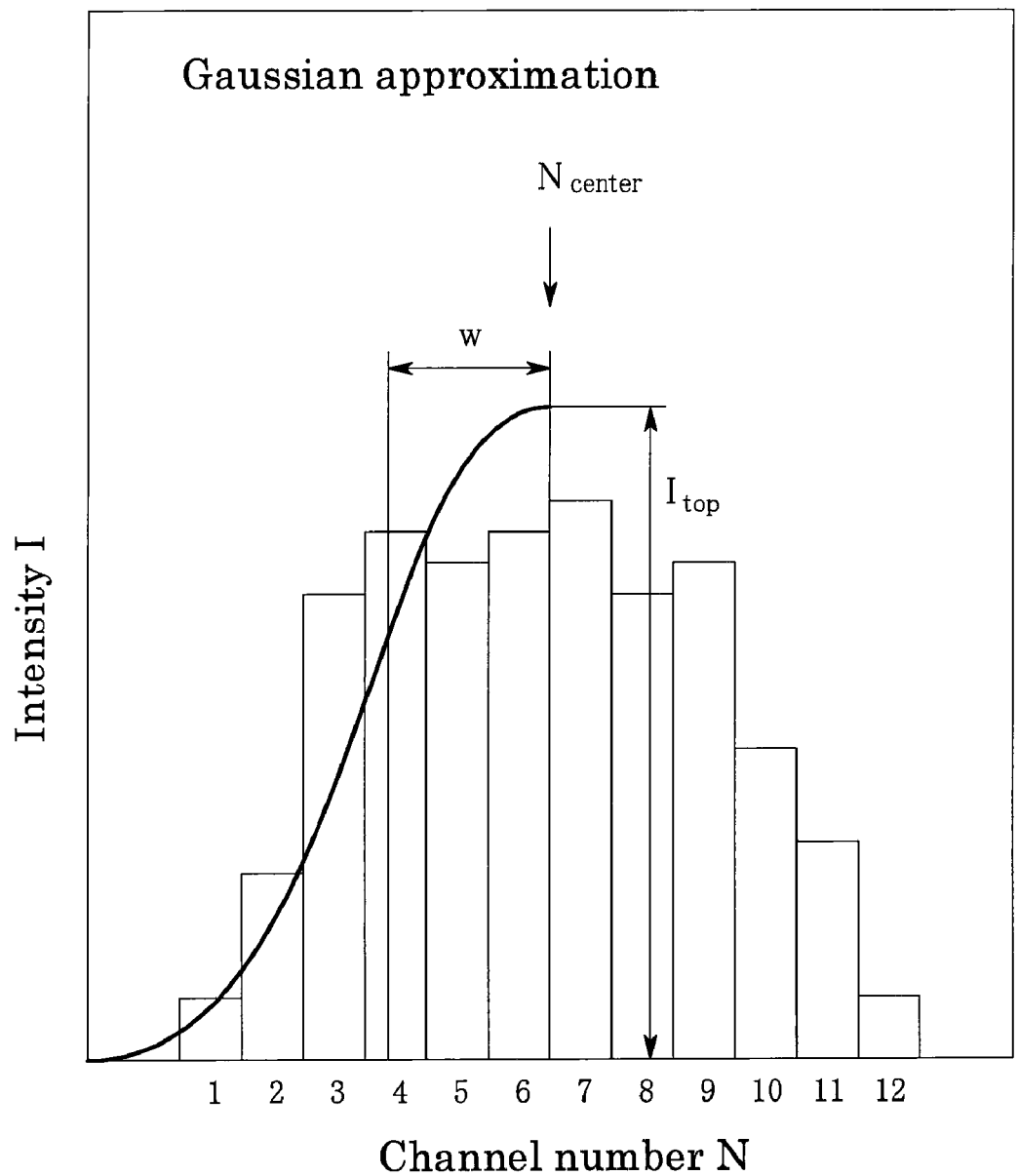
FIG. 29 shows a graph similar to FIG. 25 but for a Gaussian approximation.
Figure 30:
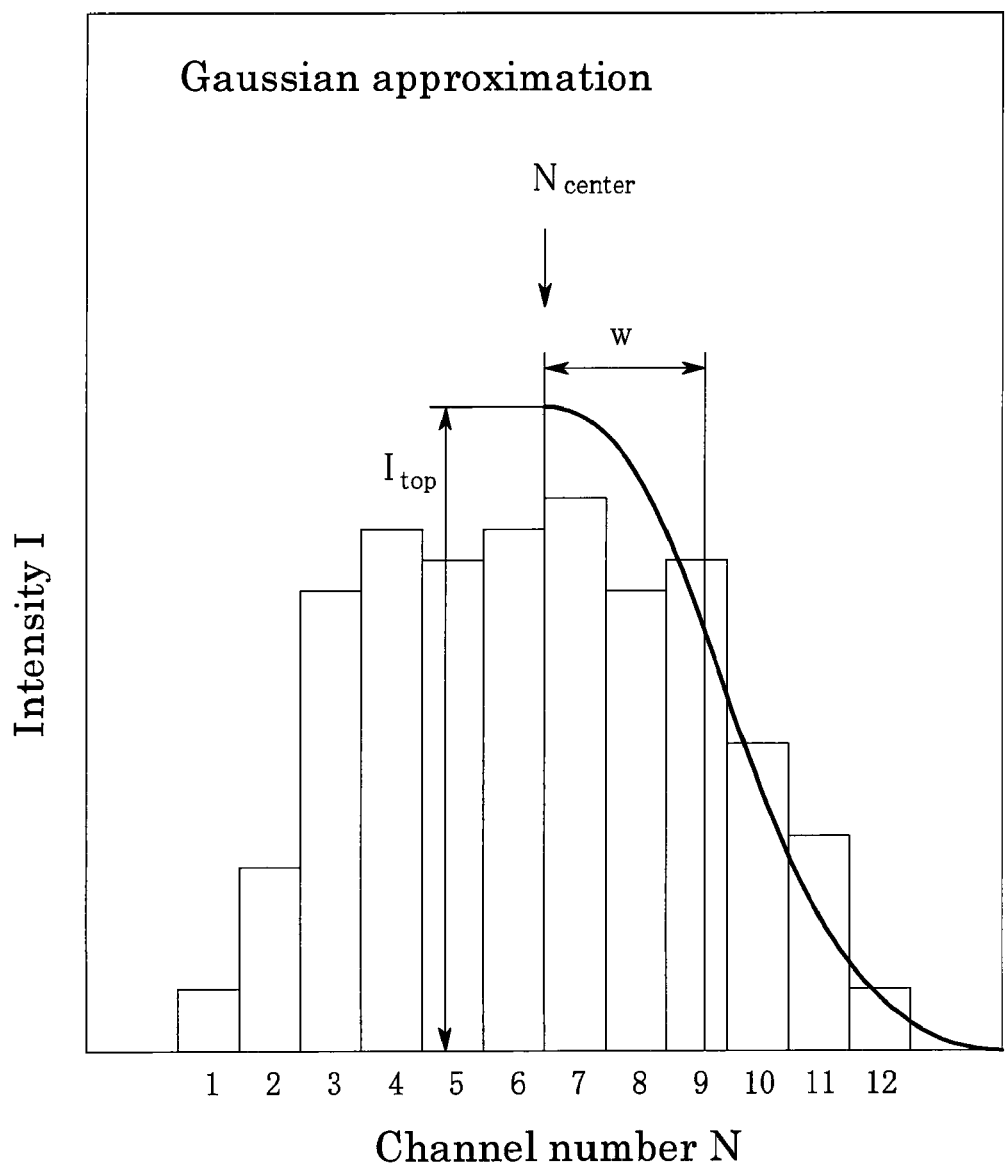
FIG. 30 shows a graph similar to FIG. 26 but for the Gaussian approximation.

FIG. 29 shows a graph that indicates a Gaussian approximation in place of the trapezoidal approximation. In the graph, the left half of the along-channels distribution of the intensities of the diffracted X-rays coming from the first crystal is under the Gaussian approximation. FIG. 30 shows a graph that indicates the Gaussian approximation of the right half of the along-channels distribution of the intensities of the diffracted X-rays coming from the tenth crystal. The respective X-ray intensities are expressed by equations (34) and (35) in FIG. 31. The target parameters in this embodiment are the three parameters BG, $I_{top}$, and w relating to the Gaussian approximation of the left half of the along-channels distribution, and the other three parameters BG, $I_{top}$, and w relating to the Gaussian approximation of the right half of the along-channels distribution. The remaining operations that should be carried out are similar to those in the trapezoidal approximation.

Figure 32:
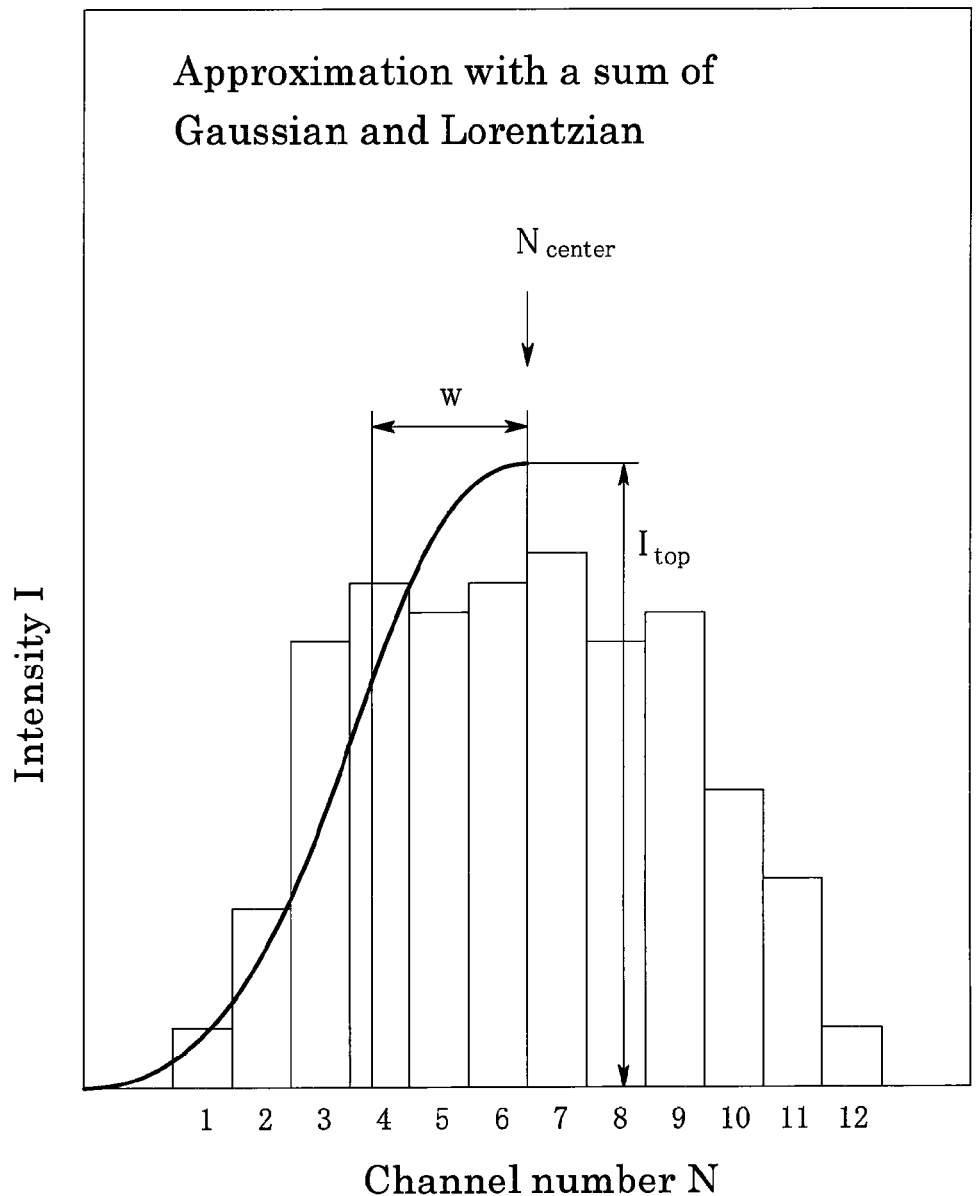
FIG. 32 shows a graph similar to FIG. 25 but for an approximation with a sum of Gaussian and Lorentzian.
Figure 33:
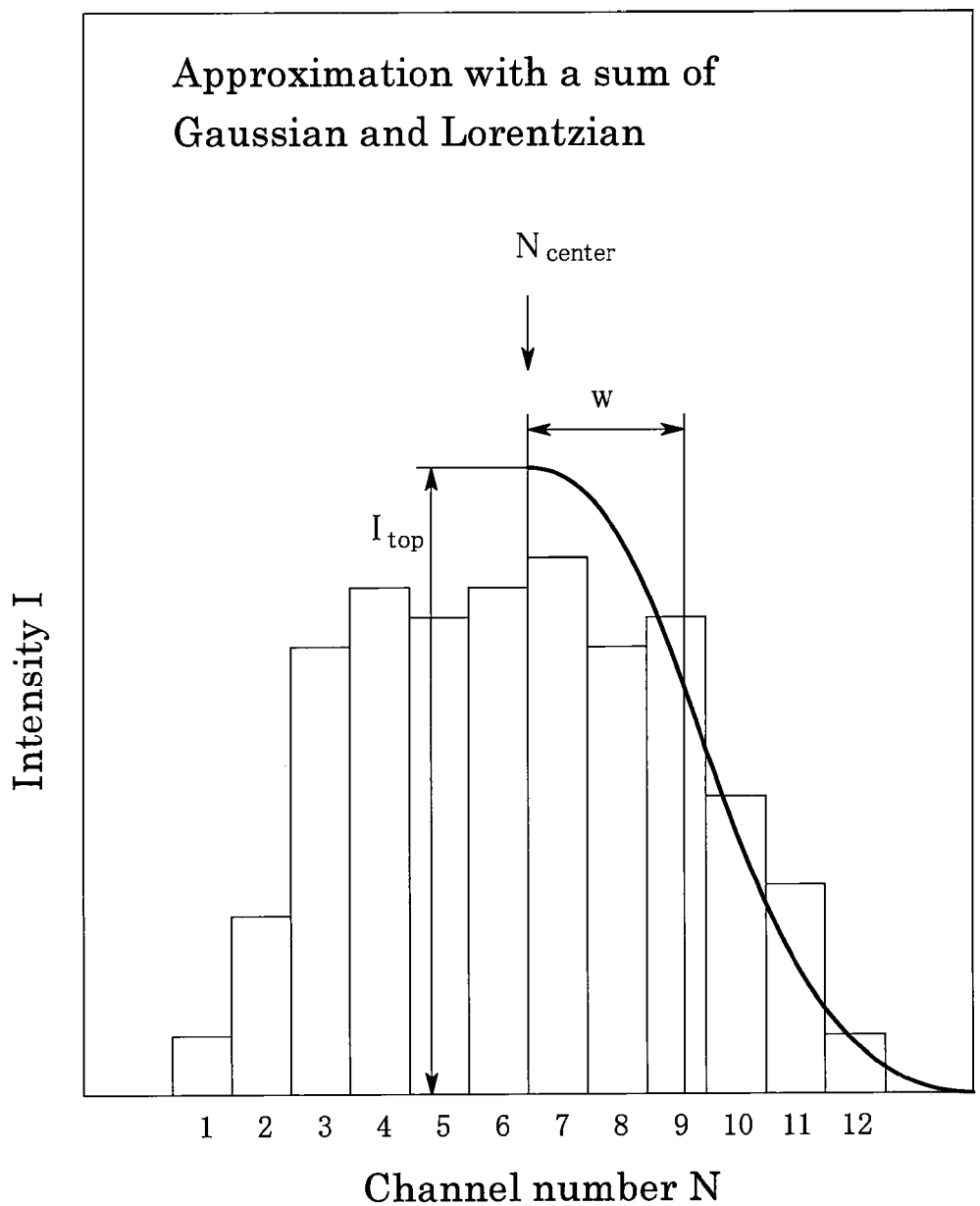
FIG. 33 shows a graph similar to FIG. 26 but for the approximation with the sum of Gaussian and Lorentzian.

FIG. 32 shows a graph indicating an approximation with a sum of Gaussian and Lorentzian. In the graph, the left half of the along-channels distribution of the intensities of the diffracted X-rays coming from the first crystal is under the approximation with a sum of the Gaussian and the Lorentzian. FIG. 33 shows a graph indicating an approximation with the similar function for the right half of the along-channels distribution of the intensities of the diffracted X-rays coming from the tenth crystal. These X-ray intensities are expressed by equations (36) and (37) in FIG. 34. The target parameters in this embodiment are the three parameters BG, $I_{top}$ and w relating to the approximation of the left half of the along-channels distribution, and the other three parameters BG, $I_{top}$ and w relating to the approximation of the right half of the along-channels distribution. The remaining operations that should be carried out are similar to those in the trapezoidal approximation.

Figure 35:
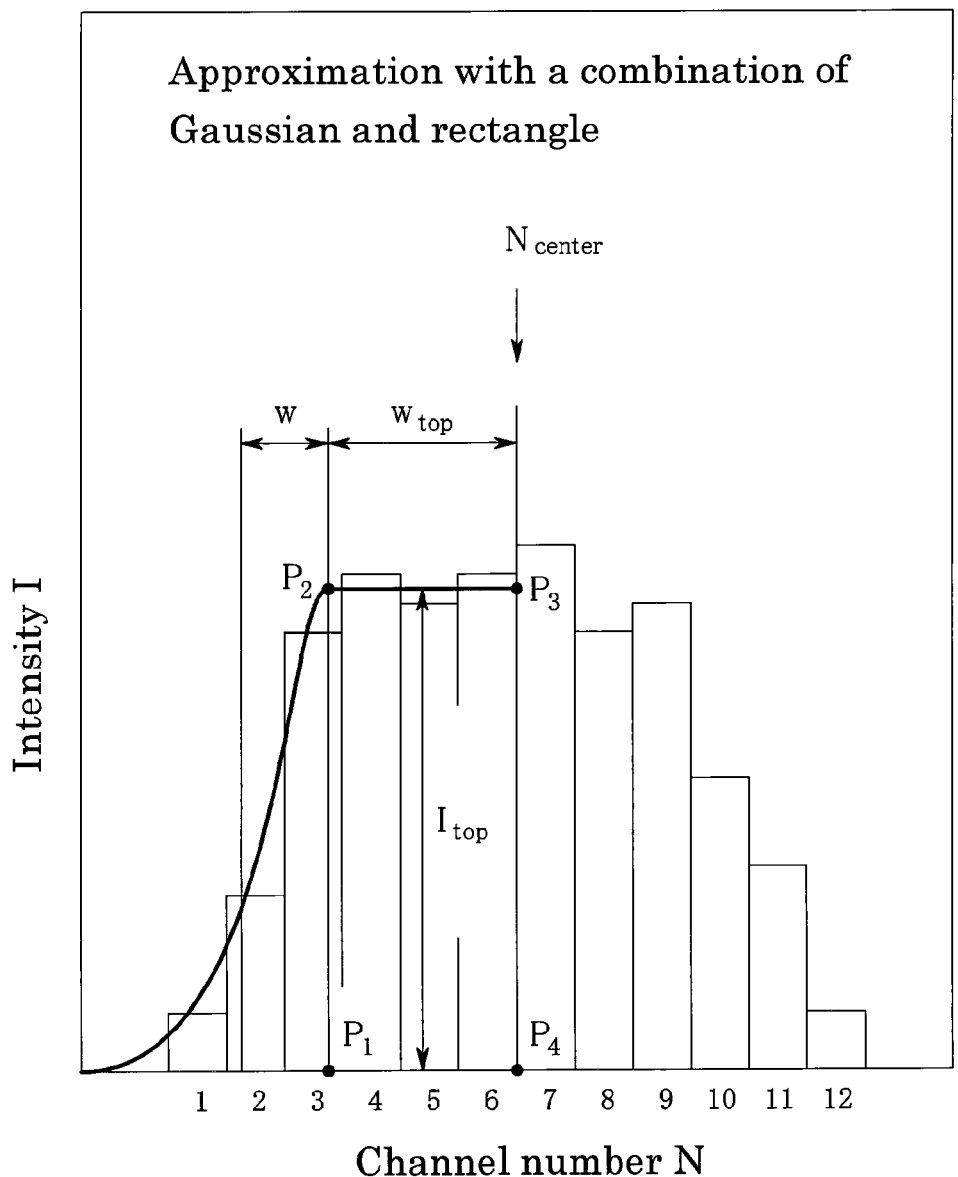
FIG. 35 shows a graph similar to FIG. 25 but for an approximation with a combination of Gaussian and a rectangle.
Figure 36:
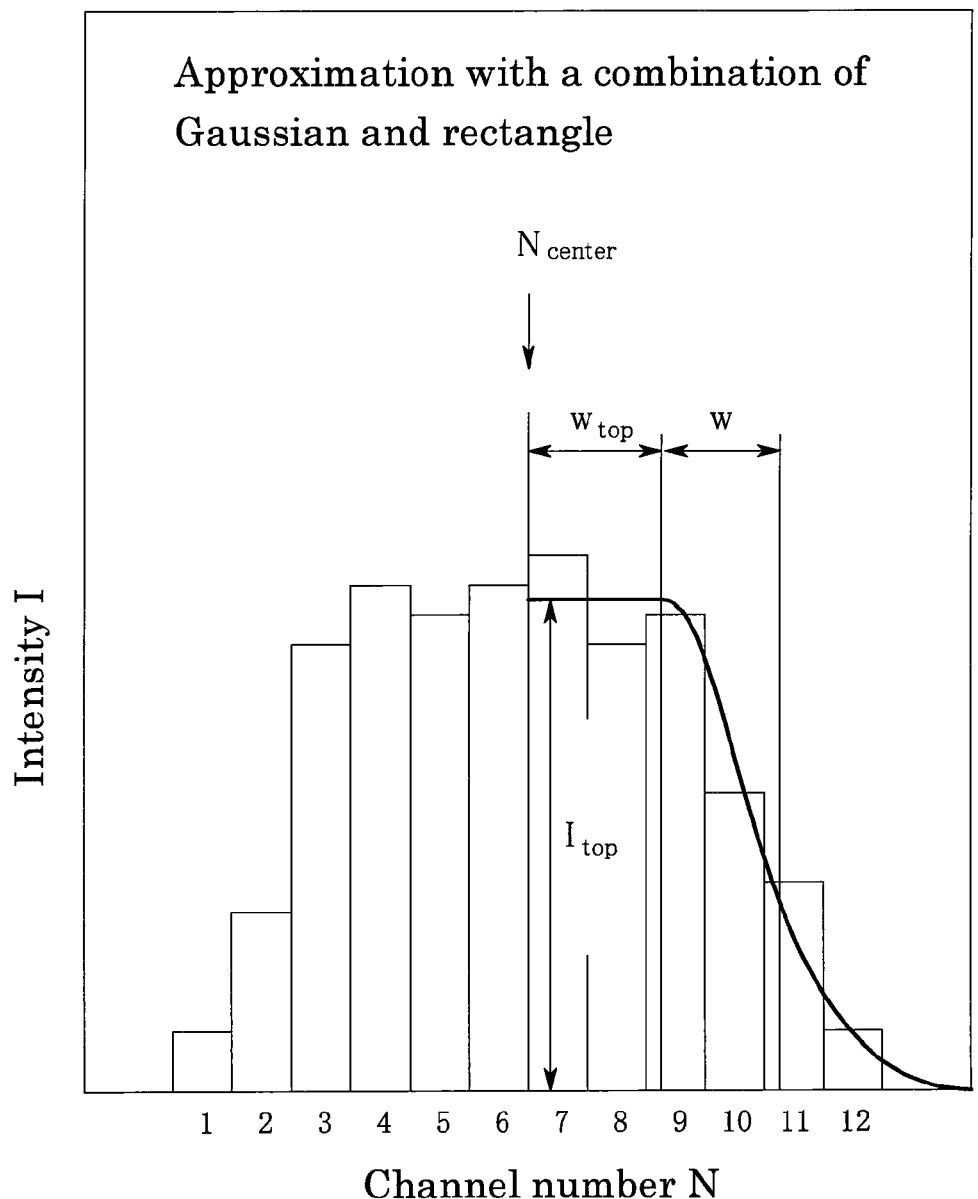
FIG. 36 shows a graph similar to FIG. 26 but for the approximation with the combination of Gaussian and the rectangle.

FIG. 35 shows a graph indicating an approximation with a combination of Gaussian and a rectangle. In the graph, the left half of the along-channels distribution of the intensities of the diffracted X-rays coming from the first crystal is under the approximation with a combination of the Gaussian and the rectangle. FIG. 36 shows a graph indicating an approximation with the similar function for the right half of the along-channels distribution of the intensities of the diffracted X-rays coming from the tenth crystal. These X-ray intensities are expressed by equations (38) to (41) in FIG. 37. The target parameters in this embodiment are the three parameters BG, $I_{top}$, $w_{top}$, and w relating to the approximation of the left half of the along-channels distribution, and the other four parameters BG, $I_{top}$, $w_{top}$, and w relating to the approximation of the right half of the along-channels distribution. The remaining operations that should be carried out are similar to those in the trapezoidal approximation.

What is claimed is:

1. An X-ray diffraction method comprising:
   a) providing an X-ray diffraction apparatus including:
      a device for generating an X-ray parallel beam, which will be incident on a sample;
      a mirror for reflecting diffracted X-rays from the sample, the mirror utilizing diffraction phenomena and the mirror having a reflective surface consisting of a combination of plural flat reflective surfaces, which are located so that an angle defined in a plane parallel to a diffraction plane becomes constant among all the flat reflective surfaces, the angle being between each flat reflective surface and a line segment connecting a center of the each flat reflective surface and the sample, and further so that a crystal lattice plane that causes reflection is parallel to each flat reflective surface; and
      an X-ray detector for detecting reflected X-rays from the mirror, the X-ray detector being one-dimensional position-sensitive in a plane parallel to the diffraction plane, wherein a relative positional relationship between the flat reflective surfaces and the X-ray detector is determined, in a plane parallel to the diffraction plane, so that reflected X-rays that have been reflected at different flat reflective surfaces reach different points on the X-ray detector respectively;
   b) allowing the X-ray parallel beam to be incident on the sample;
   c) detecting diffracted X-rays, which have been reflected at the mirror and have different diffraction angles, distinctly and simultaneously; and
   d) performing a corrective operation for separately recognizing different reflected X-rays that have been reflected at the different flat reflective surfaces and that are subject to being mixed with each other on a same detecting region of the X-ray detector;
   wherein the corrective operation is carried out based on an intensity distribution curve of the diffracted X-rays along a beam width of the diffracted X-rays, the intensity distribution curve being made in consideration of a phenomena in which X-rays are diffracted at locations also below a surface of the sample.

2. The X-ray diffraction method according to claim 1, wherein respective centers of the flat reflective surfaces are located, in a plane parallel to the diffraction plane, on an equiangular spiral having a center that is located on a surface of the sample.

3. The X-ray diffraction method according to claim 1, wherein the intensity distribution curve is made in consideration of at least one of a linear absorption coefficient of the sample, an incident angle of the X-ray parallel beam on a surface of the sample, an outgoing angle of the diffracted X-rays from the surface of the sample, a thickness of the sample, and a beam width of the X-ray parallel beam.

4. An X-ray diffraction apparatus comprising:
   a device for generating an X-ray parallel beam, which will be incident on a sample;
   a mirror for reflecting diffracted X-rays from the sample, the mirror utilizing diffraction phenomena and the mirror having a reflective surface consisting of a combination of plural flat reflective surfaces, which are located so that an angle defined in a plane parallel to a diffraction plane becomes constant among all the flat reflective surfaces, the angle being between each flat reflective surface and a line segment connecting a center of the each flat reflective surface and the sample, and further so that a crystal lattice plane that causes reflection is parallel to each flat reflective surface;
   an X-ray detector for detecting reflected X-rays from the mirror, the X-ray detector being one-dimensional position-sensitive in a plane parallel to the diffraction plane, wherein a relative positional relationship between the flat reflective surfaces and the X-ray detector is determined, in a plane parallel to the diffraction plane, so that reflected X-rays that have been reflected at different flat reflective surfaces reach different points on the X-ray detector respectively; and
   means for performing a corrective operation for separately recognizing different reflected X-rays that have been reflected at the different flat reflective surfaces and that are subject to being mixed with each other on a same detecting region of the X-ray detector;
   wherein the corrective operation is carried out based on an intensity distribution curve of the diffracted X-rays along a beam width of the diffracted X-rays, the intensity distribution curve being made in consideration of a phenomena in which X-rays are diffracted at locations also below a surface of the sample.

5. The X-ray diffraction apparatus according to claim 4, wherein respective centers of the flat reflective surfaces are located, in a plane parallel to the diffraction plane, on an equiangular spiral having a center that is located on a surface of the sample.

6. The X-ray diffraction apparatus according to claim 4, wherein the intensity distribution curve is made in consideration of at least one of a linear absorption coefficient of the sample, an incident angle of the X-ray parallel beam on a surface of the sample, an outgoing angle of the diffracted X-rays from the surface of the sample, a thickness of the sample, and a beam width of the X-ray parallel beam.

* * * * *